(12) United States Patent
Freyman

(10) Patent No.: US 6,945,957 B2
(45) Date of Patent: Sep. 20, 2005

(54) VALVE TREATMENT CATHETER AND METHODS

(75) Inventor: Toby Freyman, Watertown, MA (US)

(73) Assignee: SciMed Life Systems, Inc., Maple Grove, MN (US)

( * ) Notice: Subject to any disclaimer, the term of this patent is extended or adjusted under 35 U.S.C. 154(b) by 283 days.

(21) Appl. No.: 10/334,399

(22) Filed: Dec. 30, 2002

(65) Prior Publication Data

US 2004/0127848 A1 Jul. 1, 2004

(51) Int. Cl.$^7$ ............................................. A61M 29/00
(52) U.S. Cl. ................... 604/96.01; 604/99.02
(58) Field of Search ......................... 604/96.01, 30, 604/31, 32, 101.01, 99.02, 99.03, 99.04, 103.01, 103.03, 103.06, 103.07, 915, 916; 606/191–194

(56) References Cited

U.S. PATENT DOCUMENTS

| | | | |
|---|---|---|---|
| 3,952,747 A | 4/1976 | Kimmell, Jr. ............ 128/303 R |
| 4,705,507 A | 11/1987 | Boyles ........................ 604/101 |
| 5,091,205 A | 2/1992 | Fan ............................... 427/2 |
| 5,226,888 A | * 7/1993 | Arney .................... 604/103.07 |
| 5,469,868 A | 11/1995 | Reger ........................ 128/898 |
| 5,527,292 A | 6/1996 | Adams et al. ............. 604/171 |
| 5,538,504 A | 7/1996 | Linden et al. ................ 604/53 |
| 5,558,642 A | * 9/1996 | Schweich et al. ...... 604/103.01 |
| 5,599,307 A | * 2/1997 | Bacher et al. ......... 604/101.05 |
| 5,609,598 A | 3/1997 | Laufer et al. ............... 606/142 |
| 5,704,913 A | 1/1998 | Abele et al. ................ 604/101 |
| 5,795,325 A | 8/1998 | Valley et al. ................. 604/53 |
| 5,797,878 A | 8/1998 | Bleam ........................ 604/196 |
| 5,855,601 A | 1/1999 | Bessler et al. ................. 623/2 |
| 5,928,250 A | 7/1999 | Koike et al. ................. 606/139 |
| 5,928,281 A | 7/1999 | Huynh et al. ................... 623/2 |
| 5,931,812 A | 8/1999 | Andersen et al. ........... 604/102 |

(Continued)

OTHER PUBLICATIONS

US 6,673,110, 1/2004, Alfieri et al. (withdrawn)
US 6,723,117, 4/2004, Menz et al. (withdrawn)
"Effect of controlled adventitial heparin delivery on smooth muscle cell proliferation following endothelial injury", Edelman et al., Proc. Natl. Acad. Sci. USA, vol. 87, pp. 3773–3777, May 1990.
International Search Report, Jun. 17, 2004 (7 pgs.).

Primary Examiner—Manuel Mendez
(74) Attorney, Agent, or Firm—Brooks & Cameron PLLC

(57) ABSTRACT

The invention provides a catheter for insertion into a biological passage which contains a first flowing fluid, the catheter including a tubular member having a proximal end and a distal end; a fluid delivery lumen contained within the tubular member; an inflatable balloon assembly disposed at the distal end of the tubular member, the balloon assembly including an inflatable balloon member having an uninflated state and an inflated state, the balloon assembly including apertures in communication with the fluid delivery lumen; an inflation lumen in communication with the balloon member; and a valve contained within the inflatable balloon assembly. The inflatable balloon is assembly configured such that when the balloon member is in the inflated state: (i) sections of the balloon member contact the biological passage defining at least one containment pocket; (ii) the apertures are disposed in the containment pocket, (iii) a flow lumen is defined through the balloon member to allow the first fluid to flow through the balloon member; and (iv) the valve functions to allow the first flowing fluid to flow through the flow lumen in a physiologic direction, while blocking backflow of the first fluid through the flow lumen.

28 Claims, 9 Drawing Sheets

U.S. PATENT DOCUMENTS

| | | | |
|---|---|---|---|
| 5,948,345 A | 9/1999 | Patel et al. ................... | 264/529 |
| 5,957,949 A | 9/1999 | Leonhardt et al. ........... | 606/194 |
| 6,048,356 A | 4/2000 | Ravenscroft et al. ........ | 606/194 |
| 6,079,414 A | 6/2000 | Roth ........................... | 128/898 |
| 6,092,529 A | 7/2000 | Cox ............................ | 128/898 |
| 6,102,944 A | 8/2000 | Huynh et al. ............... | 623/2.14 |
| 6,133,631 A | 10/2000 | Belady ....................... | 623/2.17 |
| 6,165,183 A | 12/2000 | Kuehn et al. ................ | 606/139 |
| 6,165,215 A | 12/2000 | Rottenberg et al. ......... | 623/2.12 |
| 6,269,819 B1 | 8/2001 | Oz et al. ..................... | 128/898 |
| 6,306,124 B1 * | 10/2001 | Jones et al. .................. | 604/509 |
| 6,371,983 B1 | 4/2002 | Lane ........................... | 623/2.14 |
| 6,409,716 B1 | 6/2002 | Sahatjian et al. ............ | 604/509 |
| 6,425,908 B2 | 7/2002 | Ravenscroft et al. ........ | 606/194 |
| 6,436,077 B1 | 8/2002 | Davey et al. ................ | 604/247 |
| 6,666,885 B2 | 12/2003 | Moe ............................ | 623/2.12 |
| 6,666,886 B1 | 12/2003 | Tranquillo et al. .......... | 623/2.42 |
| 6,669,725 B2 | 12/2003 | Scott ........................... | 623/2.36 |
| 6,673,109 B2 | 1/2004 | Cox ............................ | 623/2.12 |
| 6,676,698 B2 | 1/2004 | McGuckin, Jr. et al. .... | 623/1.24 |
| 6,676,702 B2 | 1/2004 | Mathis ........................ | 623/2.36 |
| 6,682,558 B2 | 1/2004 | Tu et al. ...................... | 623/2.11 |
| 6,682,559 B2 | 1/2004 | Myers et al. ................. | 623/2.13 |
| 6,685,739 B2 | 2/2004 | DiMatteo et al. ............ | 623/1.24 |
| 6,692,512 B2 | 2/2004 | Jang ............................ | 606/200 |
| 6,695,878 B2 | 2/2004 | McGuckin, Jr. et al. .... | 623/1.19 |
| 6,695,886 B1 | 2/2004 | Brown et al. ................ | 606/213 |
| 6,709,456 B2 | 3/2004 | Langberg et al. ............ | 623/2.37 |
| 6,709,457 B1 | 3/2004 | Otte et al. .................... | 623/2.4 |
| 6,716,241 B2 | 4/2004 | Wilder et al. ................ | 623/1.24 |
| 6,716,244 B2 | 4/2004 | Klaco .......................... | 623/2.4 |
| 6,719,767 B1 | 4/2004 | Kimblad ...................... | 606/151 |
| 6,719,784 B2 | 4/2004 | Henderson ................... | 623/1.44 |
| 6,719,786 B2 | 4/2004 | Ryan et al. ................... | 623/2.11 |
| 6,719,787 B2 | 4/2004 | Cox ............................ | 623/2.12 |
| 6,719,788 B2 | 4/2004 | Cox ............................ | 623/2.12 |
| 6,719,789 B2 | 4/2004 | Cox ............................ | 623/2.13 |
| 6,719,790 B2 | 4/2004 | Brendzel et al. ............. | 623/2.4 |
| 6,723,038 B1 | 4/2004 | Schroeder et al. ........... | 600/16 |
| 6,723,122 B2 | 4/2004 | Yang et al. ................... | 623/2.1 |
| 6,723,123 B1 | 4/2004 | Kazatchkov et al. ......... | 623/2.2 |
| 6,726,715 B2 | 4/2004 | Sutherland ................... | 623/2.1 |
| 6,726,716 B2 | 4/2004 | Marquez ...................... | 623/2.36 |
| 6,726,717 B2 | 4/2004 | Alfieri et al. ................ | 623/2.36 |
| 6,730,118 B2 | 5/2004 | Spenser et al. ............... | 623/1.24 |
| 6,730,121 B2 | 5/2004 | Ortiz et al. ................... | 623/2.17 |
| 6,730,122 B1 | 5/2004 | Pan et al. ..................... | 623/2.33 |
| 6,736,845 B2 | 5/2004 | Marquez et al. ............. | 623/2.11 |
| 6,736,846 B2 | 5/2004 | Cox ............................ | 623/2.12 |
| 6,749,630 B2 | 6/2004 | McCarthy et al. ........... | 623/2.36 |
| 6,752,813 B2 | 6/2004 | Goldfarb et al. ............ | 606/139 |
| 6,752,828 B2 | 6/2004 | Thornton ..................... | 623/1.24 |
| 6,755,857 B2 | 6/2004 | Peterson et al. ............. | 623/2.17 |
| 6,761,734 B2 | 7/2004 | Suhr ............................ | 623/1.35 |
| 6,761,735 B2 | 7/2004 | Eberhardt et al. ............ | 623/2.1 |
| 6,764,494 B2 | 7/2004 | Menz et al. ................... | 606/159 |
| 6,764,508 B1 | 7/2004 | Roehe et al. ................. | 623/2.11 |
| 6,764,509 B2 | 7/2004 | Chinn et al. ................. | 623/2.12 |
| 6,764,510 B2 | 7/2004 | Vidlund et al. .............. | 623/2.34 |
| 6,767,362 B2 | 7/2004 | Schreck ....................... | 623/2.11 |
| 6,769,434 B2 | 8/2004 | Liddicoat et al. ............ | 128/898 |
| 6,770,083 B2 | 8/2004 | Seguin ........................ | 606/142 |
| 6,780,200 B2 | 8/2004 | Jansen ........................ | 623/2.17 |
| 6,786,924 B2 | 9/2004 | Ryan et al. ................... | 623/2.36 |
| 6,786,925 B1 | 9/2004 | Schoon et al. ............... | 623/2.38 |
| 6,790,229 B1 | 9/2004 | Berreklouw .................. | 623/2.1 |
| 6,790,230 B2 | 9/2004 | Beyersdorf et al. .......... | 623/2.18 |
| 6,790,231 B2 | 9/2004 | Liddicoat et al. ............ | 623/2.37 |
| 6,793,673 B2 | 9/2004 | Kowalsky et al. ........... | 623/2.36 |
| 6,797,000 B2 | 9/2004 | Simpson et al. ............. | 623/2.15 |
| 6,797,001 B2 | 9/2004 | Mathis et al. ................ | 623/2.37 |
| 6,797,002 B2 | 9/2004 | Spence et al. ................ | 623/2.38 |
| 6,802,860 B2 | 10/2004 | Cosgrove et al. ............ | 623/2.11 |
| 6,805,710 B2 | 10/2004 | Bolling et al. ............... | 623/2.36 |
| 6,805,711 B2 | 10/2004 | Quijano et al. .............. | 623/2.37 |
| 2002/0198558 A1 | 12/2002 | Briscoe et al. ............... | 606/192 |
| 2003/0229394 A1 | 12/2003 | Ogle et al. ................... | 623/2.14 |
| 2003/0229395 A1 | 12/2003 | Cox ............................ | 623/2.36 |
| 2003/0233142 A1 | 12/2003 | Morales et al. .............. | 623/2.37 |
| 2003/0236568 A1 | 12/2003 | Hojeibane et al. ........... | 623/1.24 |
| 2003/0236569 A1 | 12/2003 | Mathis et al. ................ | 623/1.26 |
| 2004/0002719 A1 | 1/2004 | Oz et al. ..................... | 606/142 |
| 2004/0003819 A1 | 1/2004 | St. Goar et al. ............. | 128/898 |
| 2004/0010305 A1 | 1/2004 | Alferness et al. ............ | 623/1.11 |
| 2004/0015230 A1 | 1/2004 | Moll et al. ................... | 623/1.24 |
| 2004/0015232 A1 | 1/2004 | Shu et al. ..................... | 623/2.4 |
| 2004/0015233 A1 | 1/2004 | Jansen ........................ | 623/2.18 |
| 2004/0019374 A1 | 1/2004 | Hojeibane et al. ........... | 623/1.13 |
| 2004/0019377 A1 | 1/2004 | Taylor et al. ................. | 623/2.11 |
| 2004/0019378 A1 | 1/2004 | Hlavka et al. ................ | 623/2.11 |
| 2004/0024447 A1 | 2/2004 | Haverich ..................... | 623/1.24 |
| 2004/0024451 A1 | 2/2004 | Johnson et al. .............. | 623/2.11 |
| 2004/0024452 A1 | 2/2004 | Kruse et al. .................. | 623/2.13 |
| 2004/0030321 A1 | 2/2004 | Fangrow, Jr. ................. | 604/533 |
| 2004/0030381 A1 | 2/2004 | Shu ............................. | 623/2.11 |
| 2004/0030382 A1 | 2/2004 | St. Goar et al. ............. | 623/2.36 |
| 2004/0030405 A1 | 2/2004 | Carpentier et al. .......... | 623/23.72 |
| 2004/0034380 A1 | 2/2004 | Woolfson et al. ............ | 606/170 |
| 2004/0034411 A1 | 2/2004 | Quijano et al. .............. | 623/2.11 |
| 2004/0039436 A1 | 2/2004 | Spenser et al. ............... | 623/1.13 |
| 2004/0039442 A1 | 2/2004 | St. Goar et al. ............. | 623/2.36 |
| 2004/0039443 A1 | 2/2004 | Solem et al. ................. | 623/2.37 |
| 2004/0044350 A1 | 3/2004 | Martin et al. ................ | 606/139 |
| 2004/0044365 A1 | 3/2004 | Bachman ..................... | 606/213 |
| 2004/0044403 A1 | 3/2004 | Bischoff et al. ............. | 623/1.41 |
| 2004/0049207 A1 | 3/2004 | Goldfarb et al. ............. | 606/139 |
| 2004/0049211 A1 | 3/2004 | Tremulis et al. ............. | 606/153 |
| 2004/0049266 A1 | 3/2004 | Anduiza et al. .............. | 623/2.11 |
| 2004/0059351 A1 | 3/2004 | Eigler et al. ................. | 606/148 |
| 2004/0059411 A1 | 3/2004 | Strecker ...................... | 623/1.23 |
| 2004/0059412 A1 | 3/2004 | Lytle, IV et al. ............ | 623/2.11 |
| 2004/0060161 A1 | 4/2004 | Leal et al. .................... | 29/558 |
| 2004/0073301 A1 | 4/2004 | Donlon et al. ............... | 623/2.11 |
| 2004/0073302 A1 | 4/2004 | Rourke et al. ............... | 623/2.36 |
| 2004/0078072 A1 | 4/2004 | Tu et al. ...................... | 623/1.23 |
| 2004/0078074 A1 | 4/2004 | Anderson et al. ............ | 623/2.11 |
| 2004/0082910 A1 | 4/2004 | Constantz et al. ........... | 604/101.04 |
| 2004/0082923 A1 | 4/2004 | Field ........................... | 604/267 |
| 2004/0082991 A1 | 4/2004 | Nguyen et al. ............... | 623/2.14 |
| 2004/0087975 A1 | 5/2004 | Lucatero et al. ............. | 606/139 |
| 2004/0088045 A1 | 5/2004 | Cox ............................ | 623/2.13 |
| 2004/0088046 A1 | 5/2004 | Speziali ....................... | 623/2.19 |
| 2004/0092858 A1 | 5/2004 | Wilson et al. ................ | 604/9 |
| 2004/0093060 A1 | 5/2004 | Seguin et al. ................ | 623/1.11 |
| 2004/0093070 A1 | 5/2004 | Hojeibane et al. ........... | 623/1.15 |
| 2004/0093080 A1 | 5/2004 | Helmus et al. ............... | 623/2.41 |
| 2004/0097979 A1 | 5/2004 | Svanidze et al. ............. | 606/151 |
| 2004/0098098 A1 | 5/2004 | McGuckin, Jr. et al. .... | 623/1.14 |
| 2004/0098112 A1 | 5/2004 | DiMatteo et al. ............ | 623/1.24 |
| 2004/0102839 A1 | 5/2004 | Cohn et al. ................... | 623/2.11 |
| 2004/0102840 A1 | 5/2004 | Solem et al. ................. | 623/2.11 |
| 2004/0102842 A1 | 5/2004 | Jansen ........................ | 623/2.38 |
| 2004/0106976 A1 | 6/2004 | Bailey et al. ................. | 623/1.11 |
| 2004/0106990 A1 | 6/2004 | Spence et al. ................ | 623/2.11 |
| 2004/0106991 A1 | 6/2004 | Hopkins et al. .............. | 623/2.13 |
| 2004/0111096 A1 | 6/2004 | Tu et al. ...................... | 606/108 |
| 2004/0117009 A1 | 6/2004 | Cali et al. ..................... | 623/2.12 |
| 2004/0122448 A1 | 6/2004 | Levine ........................ | 606/139 |
| 2004/0122512 A1 | 6/2004 | Navia et al. .................. | 623/2.12 |
| 2004/0122513 A1 | 6/2004 | Navia et al. .................. | 623/2.12 |
| 2004/0122514 A1 | 6/2004 | Fogarty et al. ............... | 623/2.14 |

| | | | | | | | |
|---|---|---|---|---|---|---|---|
| 2004/0122515 A1 | 6/2004 | Chu | 623/2.29 | EP | 0769272 | 8/1999 | A61B/17/04 |
| 2004/0122516 A1 | 6/2004 | Fogarty et al. | 623/2.37 | WO | WO97/29716 | 8/1997 | A61F/2/06 |
| 2004/0127979 A1 | 7/2004 | Wilson et al. | 623/2.1 | WO | WO99/00059 | 1/1999 | A61B/17/10 |
| 2004/0127980 A1 | 7/2004 | Kowalsky et al. | 623/2.11 | WO | WO99/30647 | 6/1999 | A61F/2/24 |
| 2004/0127981 A1 | 7/2004 | Rahdert et al. | 623/2.36 | WO | WO99/55405 | 11/1999 | A61M/25/00 |
| 2004/0127982 A1 | 7/2004 | Machold et al. | 623/2.36 | WO | WO00/03759 | 1/2000 | A61M/25/00 |
| 2004/0133220 A1 | 7/2004 | Lashinski et al. | 606/151 | WO | WO00/45744 | 8/2000 | A61F/2/06 |
| 2004/0133267 A1 | 7/2004 | Lane | 623/1.24 | WO | WO00/45874 | 8/2000 | A61M/1/10 |
| 2004/0133273 A1 | 7/2004 | Cox | 623/2.11 | WO | WO00/60995 | 10/2000 | A61B/17/04 |
| 2004/0138742 A1 | 7/2004 | Myers et al. | 623/2.12 | WO | WO01/36029 | 5/2001 | A61M/5/315 |
| 2004/0138743 A1 | 7/2004 | Myers et al. | 623/2.13 | WO | WO01/43808 | 6/2001 | A61M/25/00 |
| 2004/0138744 A1 | 7/2004 | Lashinski et al. | 623/2.36 | WO | WO 2004/019825 | 3/2004 | A61F/2/24 |
| 2004/0138745 A1 | 7/2004 | Macoviak et al. | 623/2.36 | WO | WO 2004/021893 | 3/2004 | A61B/17/04 |
| 2004/0148018 A1 | 7/2004 | Carpentier et al. | 623/2.18 | WO | WO 2004/023980 | 3/2004 | |
| 2004/0148019 A1 | 7/2004 | Vidlund et al. | 623/2.36 | WO | WO 2004/030568 | 4/2004 | |
| 2004/0148020 A1 | 7/2004 | Vidlund et al. | 623/2.36 | WO | WO 2004/030569 | 4/2004 | |
| 2004/0153052 A1 | 8/2004 | Mathis | 606/1 | WO | WO 2004/030570 | 4/2004 | |
| 2004/0153146 A1 | 8/2004 | Lashinski et al. | 623/2.36 | WO | WO 2004/032724 | 4/2004 | |
| 2004/0153147 A1 | 8/2004 | Mathis | 623/2.37 | WO | WO 2004/032796 | 4/2004 | |
| 2004/0158321 A1 | 8/2004 | Reuter et al. | 623/2.36 | WO | WO 2004/037128 | 5/2004 | |
| 2004/0162610 A1 | 8/2004 | Liska et al. | 623/2.11 | WO | WO 2004/037317 | 5/2004 | |
| 2004/0167539 A1 | 8/2004 | Keuhn et al. | 606/108 | WO | WO 2004/039432 | 5/2004 | |
| 2004/0167620 A1 | 8/2004 | Ortiz et al. | 623/2.11 | WO | WO 2004/043265 | 5/2004 | A61B/17/00 |
| 2004/0172046 A1 | 9/2004 | Hlavka et al. | 606/142 | WO | WO 2004/043273 | 5/2004 | A61B/17/32 |
| 2004/0176839 A1 | 9/2004 | Huynh et al. | 623/2.4 | WO | WO 2004/043293 | 5/2004 | |
| 2004/0176840 A1 | 9/2004 | Langberg et al. | 623/2.36 | WO | WO 2004/045370 | 6/2004 | |
| 2004/0181238 A1 | 9/2004 | Zarbatany et al. | 606/108 | WO | WO 2004/045378 | 6/2004 | |
| 2004/0186444 A1 | 9/2004 | Daly et al. | 604/247 | WO | WO 2004/045463 | 6/2004 | A61F/2/06 |
| 2004/0186558 A1 | 9/2004 | Pavcnik et al. | 623/1.24 | WO | WO 2004/047677 | 6/2004 | |
| 2004/0186561 A1 | 9/2004 | McGuckin, Jr. et al. | 623/1.36 | WO | WO 2004/060217 | 7/2004 | A61F/2/24 |
| 2004/0186563 A1 | 9/2004 | Iobbi | 623/2.11 | WO | WO 2004/060470 | 7/2004 | A61M/25/10 |
| 2004/0186565 A1 | 9/2004 | Schreck | 623/2.18 | WO | WO 2004/062725 | 7/2004 | A61N/1/362 |
| 2004/0186566 A1 | 9/2004 | Hindrichs et al. | 623/2.37 | WO | WO 2004/066803 | 8/2004 | |
| 2004/0193191 A1 | 9/2004 | Starksen et al. | 606/153 | WO | WO 2004/066826 | 8/2004 | |
| 2004/0193253 A1 | 9/2004 | Thorpe et al. | 623/1.24 | WO | WO 2004/069287 | 8/2004 | |
| 2004/0193260 A1 | 9/2004 | Alferness et al. | 623/2.11 | WO | WO2004/075789 | 9/2004 | A61F/2/02 |
| 2004/0199155 A1 | 10/2004 | Mollenauer | 606/27 | WO | WO2004/080352 | 9/2004 | A61F/2/24 |
| 2004/0199183 A1 | 10/2004 | Oz et al. | 606/142 | WO | WO2004/082523 | 9/2004 | |
| 2004/0199191 A1 | 10/2004 | Schwartz | 606/159 | WO | WO2004/082527 | 9/2004 | |
| 2004/0204758 A1 | 10/2004 | Eberhardt et al. | 623/2.15 | WO | WO2004/082528 | 9/2004 | |
| 2004/0206363 A1 | 10/2004 | McCarthy et al. | 128/898 | WO | WO2004/082536 | 9/2004 | A61F/2/24 |
| 2004/0210240 A1 | 10/2004 | Saint | 606/139 | WO | WO2004/082537 | 9/2004 | A61F/2/24 |
| 2004/0210301 A1 | 10/2004 | Obermiller | 623/1.24 | WO | WO2004/082538 | 9/2004 | A61F/2/24 |
| 2004/0210303 A1 | 10/2004 | Sedransk | 623/2.1 | WO | WO2004/082757 | 9/2004 | A61M/39/24 |
| 2004/0210304 A1 | 10/2004 | Seguin et al. | 623/2.11 | WO | WO 2004/084746 | 10/2004 | A61B/18/00 |
| 2004/0210305 A1 | 10/2004 | Shu et al. | 623/2.11 | WO | WO 2004/084770 | 10/2004 | A61F/2/06 |
| 2004/0210306 A1 | 10/2004 | Quijano et al. | 623/2.17 | WO | WO 2004/089246 | 10/2004 | A61F/2/00 |
| 2004/0210307 A1 | 10/2004 | Khairkhahan | 623/2.18 | WO | WO 2004/089250 | 10/2004 | A61F/2/06 |
| 2004/0215333 A1 | 10/2004 | Duran et al. | 623/1.24 | WO | WO 2004/089253 | 10/2004 | A61F/2/24 |
| 2004/0215339 A1 | 10/2004 | Drasler et al. | 623/3.1 | WO | WO 2004/091449 | 10/2004 | A61F/2/06 |
| | | | | WO | WO 2004/091454 | 10/2004 | A61F/2/24 |

FOREIGN PATENT DOCUMENTS

| EP | 0362113 | 4/1993 | A61F/2/24 |
|---|---|---|---|

\* cited by examiner

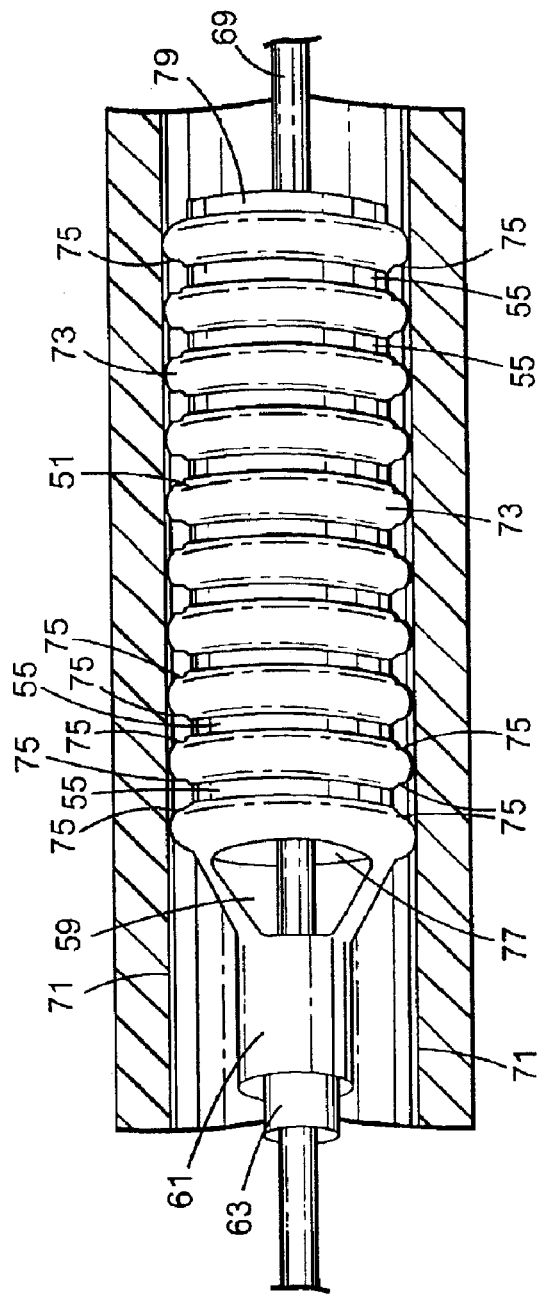
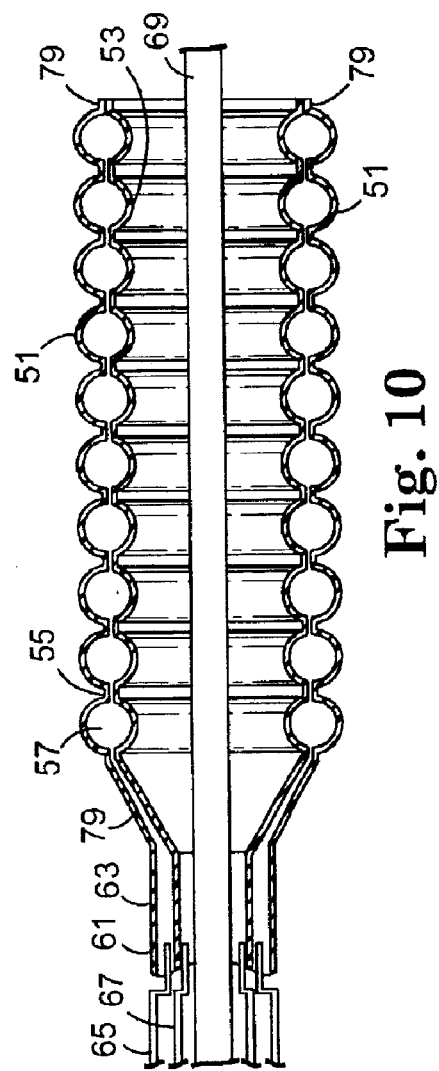
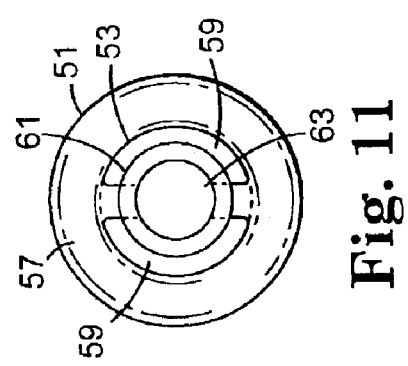

VALVE TREATMENT CATHETER AND METHODS

FIELD OF THE INVENTION

The invention relates to treatment of a biological passage containing a valve. More particularly, the invention provides a catheter having a blood flow lumen containing a valve that mimics the native valve to be treated. The valve of the inventive device permits blood flow in a physiologic direction while blocking backflow.

BACKGROUND OF THE INVENTION

Heart valve disease is a serious health problem facing society today. There are approximately 225,000 surgeries annually to repair damaged heart valves. Of these surgeries, at least 60,000 Americans receive replacements for valves damaged by congenital or rheumatic heart disease.

Cardiac valves have three functional properties: (1) preventing regurgitation of blood flow (also referred to as retrograde flow, or backflow) from one chamber to another, (2) permitting rapid flow of blood without imposing resistance on that flow, and (3) withstanding high-pressure loads. Importantly, all four of the heart valves are passive structures in that they do not themselves expend any energy and do not perform any active contractile function. They consist of movable leaflets that are designed simply to open and close in response to differential pressures on either side of the valve. Fluid flows from areas of high pressure to areas of low pressure. In the heart, the valves open and close in response to pressure gradients; that is, valves open when pressure in the preceding chamber is higher and close when the gradient reverses.

Because proper valve function is an important aspect of the present disclosure, basic cardiac physiology will be described in some detail with reference to FIGS. 1 and 2. FIG. 1 shows a cross-sectional cutaway depiction of a normal human heart 91. The left side of the heart 91 contains left atrium 93, left ventricular chamber 95 positioned between left ventricular wall 97 and septum 99, aortic valve 101, and mitral valve assembly 103. The components of the mitral valve assembly 103 include the mitral valve annulus 105, anterior leaflet 107 (sometimes referred to as the aortic leaflet, since it is adjacent to the aortic region), posterior leaflet 109, two papillary muscles 111 and 113, and multiple chordae tendineae 115. The papillary muscles 111 and 113 are attached at their bases to the interior surface of the left ventricular wall 97. The chordae tendineae 115 couple the mitral valve leaflets 107 and 109 to the papillary muscles 111 and 113, and these cords support the mitral valve leaflets and control or restrict leaflet motion.

The right side of the heart contains the right atrium 121, a right ventricular chamber 123 bounded by right ventricular wall 125 and septum 99, and a tricuspid valve assembly 127. The tricuspid valve assembly 127 comprises a valve annulus 129, three leaflets 131, papillary muscles 133 attached to the interior surface of the right ventricular wall 125, and multiple chordae tendineae 135. The chordae tendineae 135 couple the tricuspid valve leaflets 131 to the papillary muscles 133 and serve similar function as for the mitral valve leaflets.

Turning to the two cardiac valves that function to permit blood flow out of the heart to the lungs (the pulmonary valve) or to the aorta (aortic valve), reference will now be made to FIG. 2. FIG. 2 shows a cross-sectional cutaway depiction of a normal heart 91, illustrating the four valves of the heart, namely the mitral valve assembly 103, tricuspid valve assembly 127, pulmonary valve 151, and aortic valve 161. The aortic valve 161 and pulmonary valve 151 are referred to as semilunar valves because of the unique appearance of their leaflets, which are more aptly termed cusps and are shaped like a half-moon. Each of the semilunar valves includes three cusps, and neither of the valves includes associated chordae tendineae or papillary muscles.

The aortic valve includes cusps 163, 165, and 167 that respond to pressure differentials between the left ventricle and the aorta. When the left ventricle contracts, the aortic valve cusps 163, 165 and 167 open to allow the flow of oxygenated blood from the left ventricle into the aorta. When the left ventricle relaxes, the aortic valve cusps reapproximate to prevent the blood that has entered the aorta from leaking (regurgitating) back into the left ventricle. The pulmonary valve includes cusps 153, 155, and 157 that respond passively in the same manner in response to relaxation and contraction of the right ventricle in moving de-oxygenated blood into the pulmonary artery and thence to the lungs for re-oxygenation.

The valves in the heart thus maintain the physiologic direction of blood flow, namely: right atrium-right ventricle-lungs-left atrium-left ventricle-aorta. Although each of these valves has slightly different structure, they serve similar functions. When the ventricle expands, the atrioventricular valve allows blood to flow forward from the atrium into the ventricle while the semilunar valve keeps blood that has already been pumped out of the heart from flowing back in. Conversely, when the ventricle contracts, the atrioventricular valve closes to prevent backflow while the semilunar valve opens to allow blood to be pumped either to the body or the lungs. The prevention of backflow ensures the proper direction of flow through the circulatory system and reduces the amount of work the heart must do to pump blood through the system.

There are numerous complications and diseases of the heart valves that can prevent the proper flow of blood. Heart valve disease can be classified into one of two categories: stenosis (or hardening of the valve), and incompetence (or permittence of backflow). Stenotic valves cannot open fully, requiring more work to push the liquid through the valve. By contrast, incompetent valves waste work by allowing blood to flow backward (backflow). As a result of stenosis or incompetence, the heart must work harder to provide the same level of blood circulation, and in many cases the heart becomes incapable of sustaining an active lifestyle.

Though the causes of heart valve disease are numerous, there are three principal culprits. Rheumatic fever stiffens valve tissue, causing stenosis. Congenitally defective valves do not form properly as the heart develops, but often go unnoticed until adulthood. Bacterial infection of the heart can cause inflammation of valves, tissue scarring, or permanent degradation. Many of these damaged valves have to be replaced in order for the patient to live a normal life, since the strain on their heart would otherwise cause such symptoms as chest pain, fatigue, shortness of breath, and fluid retention.

Once a cardiac valve is damaged, treatment options include replacement of the damaged valve or pharmacologic intervention. Current options for replacing heart valves include mechanical prosthetics, bioprosthetics, and transplants. While each of these options has benefits, there are drawbacks associated with each.

Mechanical prosthetic heart valves mimic the function of natural heart valves with a variety of artificial structures. The majority of current mechanical valve designs, and those that are considered closest to native valves, constitute bileaflet valves. These valves consist of two semicircular leaflets (often fabricated from carbon) that pivot on hinges. The carbon leaflets exhibit high strength and excellent biocompatibility. The leaflets open completely, parallel to the direction of blood flow. However, the mechanical leaflets do not close completely, which allows some backflow. Since backflow is one of the properties of defective valves, the bileaflet valves are still not ideal valves. As a result of the less-than-ideal flow properties of the valve, these valves can cause the heart to work harder to pump blood. The resulting stress on the heart can damage heart muscle and blood cells in the vicinity of the valve. In addition, mechanical valves can cause thrombosis, or blood clot formation, and serve as excellent substrates for bacterial infection. Thus, recipients of these medical valves are often required to take anticoagulants, or blood clot inhibitors, for the rest of their lives.

Although effective for short relatively short periods (typically ten to fifteen years), bioprosthetic valves offer a second alternative for successfully replacing human valves. Generally, bioprosthetic valves are valves made from tissue harvested from other mammals. The most commonly used animal tissues for bioprosthetic valves are porcine (pig) and bovine (cow) pericardial tissue. The harvested porcine or bovine tissue is treated with a fixative (often glutaraldehyde) before implantation. The most common cause of bioprosthesis failure is stiffening of the tissue due to the build up of calcium. Calcification can cause a restriction of blood flow through the valve (stenosis) or cause tears in the valve leaflets, thereby requiring a subsequent valve replacement. Further, bioprosthetics generally do not integrate well with the host organism and eventually die.

The third alternative is a transplant from a human organ donor. In this case, the replacement valve becomes a living part of the surrounding heart tissue, if it can overcome the initial immune system rejection seen in all human-to-human transplants. However, this alternative is not commonly seen, since most available human hearts are directed to whole-heart transplants, rather than valve-only transplants.

The alternative to replacement of the damaged valve is treatment of the valve with therapeutic agents. Delivery of a therapeutic agent to the valve tissue can result in improved valve function, and correspondingly, improved heart function. Generally, pharmacologic treatment is systemic. That is, a therapeutic agent is orally or intravenously injected into the patient and is therefore delivered throughout the patient's entire body. In the case of systemic treatment, high concentrations of the therapeutic agent cannot be used in many cases, because of risk of undesirable side effects.

Thus, current treatment options for heart valve disease have several drawbacks. Damaged or diseased heart valves can be replaced with one of several different types of prosthetic valves. These prosthetic valves must create a non-return flow system and must meet certain standards with regard to strength and durability, since the human body is a harsh place for foreign objects. Alternatively, damaged or diseased heart valves can be treated with therapeutic agents. Although therapeutic treatment is a preferred alternative to outright replacement of the valve, risks associated with systemic exposure to the therapeutic agent(s) must be taken into consideration.

For treating vessel walls, a flow through catheter has been developed that merely provides flow through while exposing the vessel walls to a therapeutic agent. U.S. Pat. No. 5,558,642 (the entire disclosure of which is incorporated herein by reference) describes a drug delivery catheter that can be inserted into a vessel, such as a blood vessel. The drug delivery catheter comprises an elongated tubular shaft that includes a drug lumen for delivering a drug to the treatment site and a uniquely configured inflatable balloon assembly. The balloon assembly is disposed at the distal end of the shaft and includes an inflatable balloon member. The balloon member has a configuration such that when the balloon member is uninflated, the fluid in the vessel (such as blood) may flow around the balloon assembly. This provides an arrangement that may be easily inserted and manipulated through the vascular system. When the balloon member is in an inflated state, part of the balloon member contacts the vessel wall defining a containment pocket between the vessel wall and the balloon assembly. The balloon assembly includes apertures in the containment pocket that are in fluid communication with a drug lumen in order to provide the drug to the containment pocket. A flow lumen is also defined through the balloon member when it is inflated in order to allow the fluid in the vessel, such as blood, to flow through the balloon assembly. The catheter also includes an inflation lumen that is used to inflate the balloon member.

SUMMARY OF THE INVENTION

In one aspect, the invention provides a catheter for insertion into a biological passage which contains a first flowing fluid, the catheter comprising: a tubular member having a proximal end and a distal end; a fluid delivery lumen contained within the tubular member; an inflatable balloon assembly disposed at the distal end of the tubular member, the balloon assembly including an inflatable balloon member having an uninflated state and an inflated state, the balloon assembly including apertures in communication with the fluid delivery lumen; an inflation lumen in communication with the balloon member; and a valve contained within the inflatable balloon assembly. According to the invention, the inflatable balloon assembly is configured such that when the balloon member is in the inflated state: (i) sections of the balloon member contact the biological passage defining at least one containment pocket; (ii) the apertures are disposed in the containment pocket, (iii) a flow lumen is defined through the balloon member to allow the first fluid to flow through the balloon member; and (iv) the valve functions to allow the first flowing fluid to flow through the flow lumen in a physiologic direction, while blocking backflow of the first fluid through the flow lumen.

In another aspect, the invention provides a catheter for insertion into a biological passage which contains a first flowing fluid, the catheter comprising: a tubular member having a proximal end and a distal end; an inflatable balloon assembly disposed at the distal end of the tubular member, the balloon assembly including an inflatable balloon member having an uninflated state and an inflated state; an inflation lumen in communication with the balloon member; and a valve contained within the inflatable balloon assembly. According to this aspect, the inflatable balloon assembly is configured such that when the balloon member is in the inflated state: (i) sections of the balloon member contact the biological passage defining at least one containment pocket; (ii) a flow lumen is defined through the balloon member to allow the first fluid to flow through the balloon member; and (iii) the valve functions to allow the first flowing fluid to flow through the flow lumen in a physiologic direction, while blocking backflow of the first fluid through the flow lumen.

In yet another aspect, the invention provides a catheter for insertion into a biological passage which contains a first flowing fluid, the catheter comprising: a tubular member having a proximal end and a distal end; a fluid delivery lumen contained within the tubular member; an inflatable balloon assembly comprising a first toroidal-shaped balloon disposed at the distal end of the tubular shaft, a second toroidal-shaped balloon spaced proximally from the first toroidal-shaped balloon, and a cylindrical sheath attached to the first and second toroidal-shaped balloons, wherein the first and second toroidal shaped balloons have an outer diameter, and wherein the sheath is attached to the toroidal-shaped balloons at a position radially inward of the outer diameter of the toroidal-shaped balloons; an inflation lumen in communication with the toroidal-shaped balloons; and a valve contained within the sheath, wherein the inflatable balloon assembly is configured such that when the toroidal-shaped balloons are inflated: (i) the toroidal-shaped balloons expand the sheath, (ii) sections of the toroidal-shaped balloons contact the biological passage wall defining at least one containment pocket between the biological passage, the tubular shaft, the toroidal-shaped balloons, and the sheath; (iii) the apertures are disposed in the containment pocket, (iv) the sheath forms a flow lumen to allow the first fluid to flow through the balloon member; and (v) the valve functions to allow the first flowing fluid to flow through the flow lumen in a physiologic direction, while blocking backflow of the first fluid through the flow lumen.

In yet another aspect, the invention provides a method of delivering a therapeutic fluid to a treatment site in a biological passage, the treatment site including a valve, the biological passage containing a first fluid, the method comprising steps of: providing an inflatable balloon assembly on the distal end of a catheter, the size of the balloon assembly when deflated adapted to fit within the biological passage; positioning the balloon assembly at the treatment site; inflating the balloon assembly at the treatment site; engaging a section of the biological passage with a section of the balloon assembly while maintaining a section of the balloon assembly away from the biological passage thereby defining a plurality of containment pockets within the engaging section; and delivering a therapeutic fluid to the containment pockets, wherein when the balloon assembly is inflated, the balloon assembly defines a flow lumen through which the first fluid can flow, while maintaining the therapeutic fluid within the containment pockets, and a valve contained within the balloon assembly functions to allow the first flowing fluid to flow through the balloon member in a physiologic direction, while blocking backflow of the first fluid through the balloon member.

The invention provides improved devices and methods for effectively treating a biological passage containing a valve. Preferred embodiments of the invention can be advantageously used to provide flexibility in treatment duration and type of therapeutic agent delivered capable of being delivered to a native valve.

BRIEF DESCRIPTION OF THE DRAWINGS

The accompanying drawings, which are incorporated in and constitute a part of this specification, illustrate several aspects of the invention and together with the description of the preferred embodiments, serve to explain the principles of the invention. A brief description of the drawings is as follows:

FIG. 9 is a side view of an embodiment of the invention.

FIG. 10 is a cross-sectional view of the embodiment shown in FIG. 9.

FIG. 11 shows a front view of the embodiment shown in FIG. 9.

DETAILED DESCRIPTION OF THE INVENTION

Figure 1:
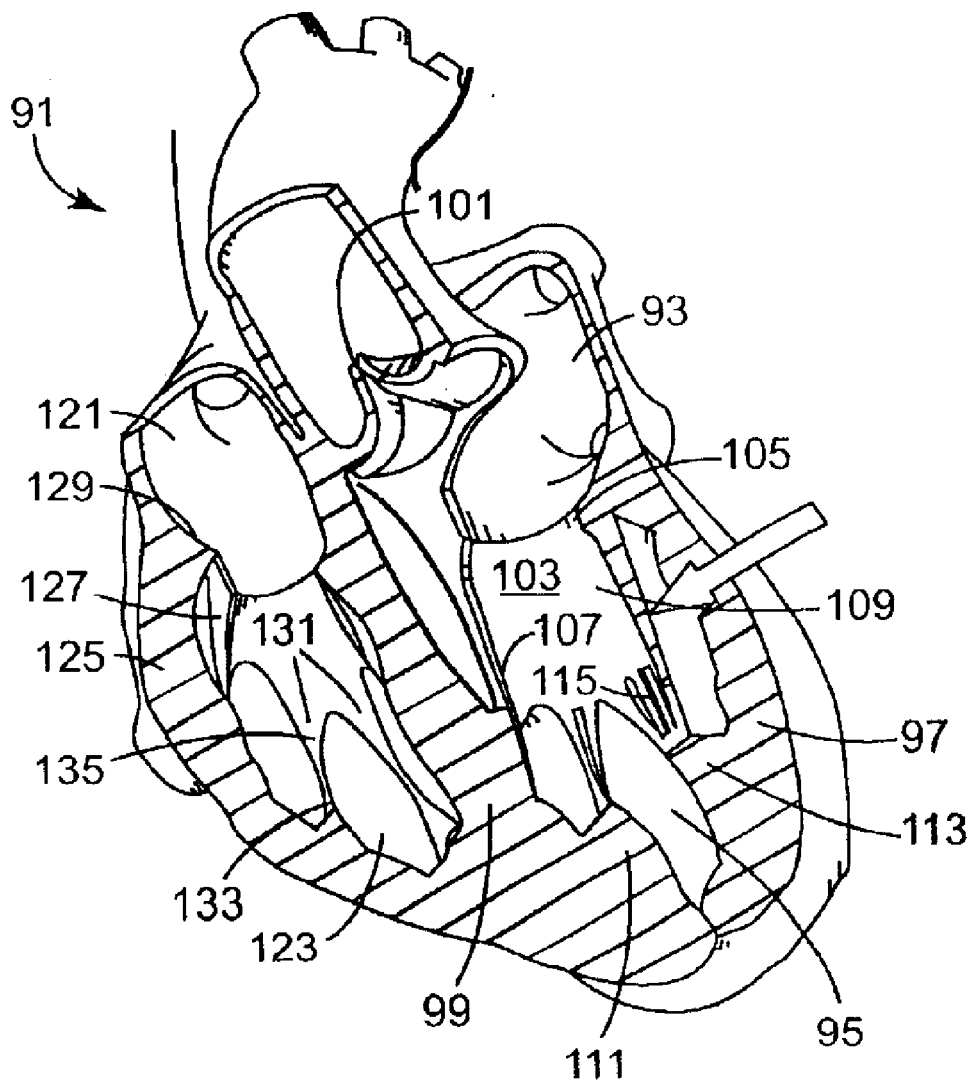
FIG. 1 is a cross-sectional view of a normal human heart.
Figure 2:
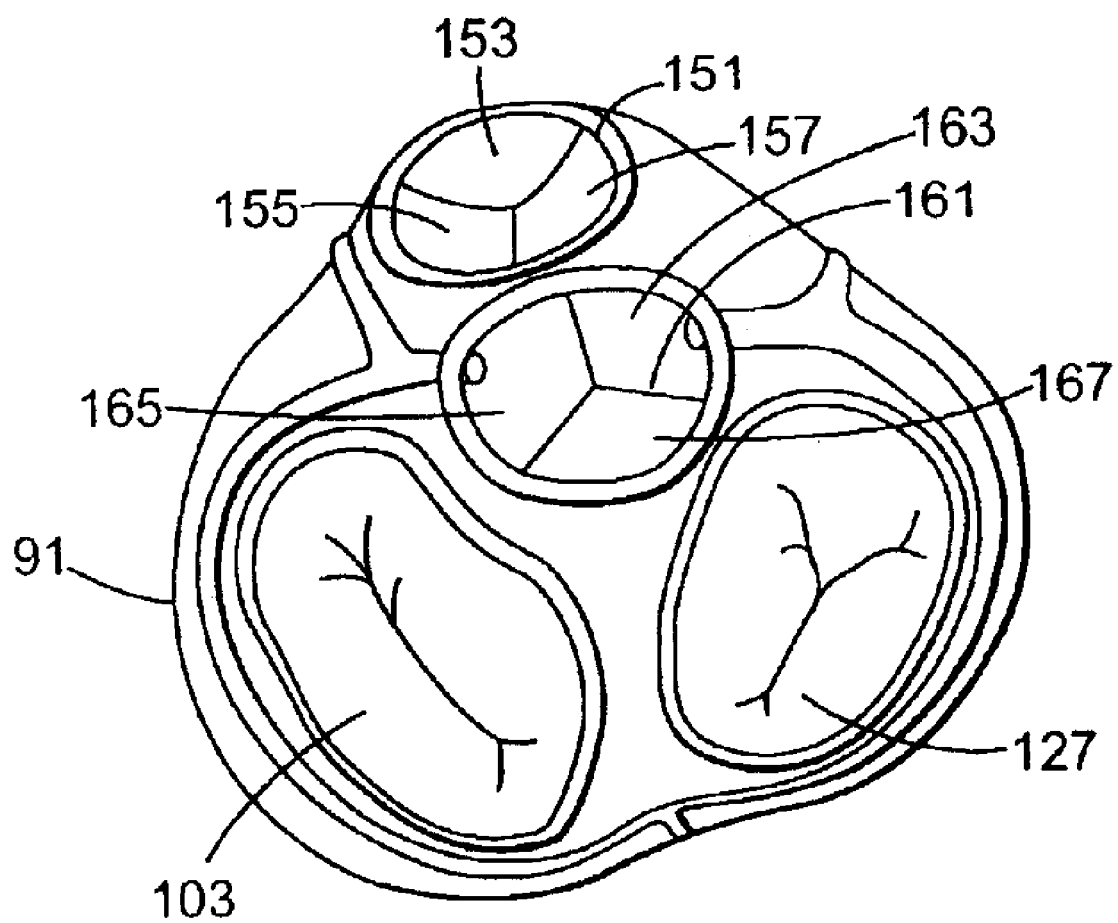
FIG. 2 is a cross-sectional view of a normal human heart, illustrating the four heart valves.

The embodiments of the present invention described below are not intended to be exhaustive or to limit the invention to the precise forms disclosed in the following detailed description. Rather, the embodiments are chosen and described so that others skilled in the art can appreciate and understand the principles and practices of the present invention.

The present invention is directed to methods and apparatuses for effectively treating a biological passage, and in particular for delivering therapeutic agents to a valve within a biological passage. Such methods and apparatuses in accordance with the present invention can advantageously be used to provide flexibility in treatment duration and type of therapeutic agent delivered to the valve. In particular, the present invention has been developed for delivering one or more therapeutic agents to a valve while maintaining blood flow through the biological passage in a physiologic manner. Such devices (for example, catheters), themselves, are known for treating problems and diseases of the body in that they are made for introduction within any number of body passages or lumens, such as are provided within the vascular, urinary, respiratory, esophageal, gastrointestinal systems of the body and the like. Therapeutic catheterization techniques (whether for treatment of a site or for diagnostic purposes) can involve the use of a guide wire that is first controllably inserted within the body up to and beyond the treatment site within the body lumen. Thus, in order to follow such a guide wire to a treatment site, catheter lumens have been developed that comprise one or more tubular components that can be slid along the guide wire to the appropriate treatment site. As used throughout this disclosure, a treatment site can comprise a site that is to receive treatment directly or indirectly from a catheter component or any site that is being diagnosed directly or indirectly by a catheter component.

For example, a balloon catheter for intravascular treatment is typically delivered along a guide wire. Balloon catheters are well known, such as are described in U.S. Pat.

No. 5,797,878, U.S. Pat. No. 5,931,812 and U.S. Pat. No. 5,948,345, the entire disclosures of which are incorporated herein by reference. A typical balloon catheter has an elongate shaft with an inner tubular lumen and has a dilatation balloon attached proximate the distal end and a manifold attached proximate the proximal end. These catheters are designed for introduction into a body lumen over the guide wire, which guide wire is slidably received within the inner lumen of the catheter. In use, the balloon catheter is advanced over the guide wire such that the dilatation balloon is positioned adjacent a treatment site, such as an occlusion or any obstruction, lesion, or stenosis of a body lumen. Then, fluid under pressure is supplied to the balloon through the catheter lumen, expanding the balloon and thus applying a force to the wall of the body lumen, such as for opening or otherwise treating or diagnosing it.

In order to be properly introduced, delivered and controlled, catheters of all sorts of types are preferably designed to accommodate needs for pushability, trackability, crossability and torque transmission to the distal catheter end as such is applied to the proximal end of the catheter. For purposes of this application, the following terms are given the following meaning. Pushability is the ability to transmit force from the proximal end of the catheter to the distal end of the catheter. A catheter shaft should have adequate strength for pushability and resistance to buckling or kinking. Trackability is the ability to navigate tortuous vasculature or other body lumens. That is, the distal portion of the catheter must track the guide wire through small tortuous vessels or body lumens to reach the area to be treated. A more flexible distal portion is known to improve trackability. Thus, it can be desirable to provide a catheter shaft with elastomeric properties to improve flexibility. Crossability is the ability to navigate the balloon catheter across narrow restrictions or obstructions in the vasculature.

Optimization of pushability, trackability, crossability and torque transmission can be accomplished by carefully choosing the catheter material and its physical characteristics, such as wall thickness. Because these catheters are frequently inserted for long distances, it is generally also desirable to minimize the friction between the guide wire and the surface of the catheter lumen by constructing the catheter from a lubricious material such as a high-density polyethylene (HDPE), polytetrafluoroethylene (PTFE) or similar material. Polymeric materials are known for these uses.

In order to achieve a combination of desired properties at different parts of the catheters themselves, catheters have been developed by combining a plurality of tubing components together to define a catheter lumen. That is, a portion of the overall length of a catheter lumen can comprise a different tubing type component than another. These one or more portions can comprise tubing components of different physical characteristics and/or different materials. For example, a tip portion can be provided that is more resilient than the remainder of the catheter lumen for better crossability and to provide a softer leading end of the catheter for abutting internal membranes of the body and the like. Different materials include different polymeric materials from one another, for example, or similar polymers of different densities, fillers, crosslinking or other characteristics. In particular, a portion of a catheter lumen can comprise a material chosen for flexibility to follow a body lumen's path while another portion can comprise a material chosen for axial and/or torque transmission.

Likewise, other catheter features, such as balloons, are frequently prepared from a variety of polymeric materials depending upon their intended use. Generally, materials for balloons, for example, are required to possess elastomeric properties so that the dilatation balloon has the requisite compliance to achieve a predetermined relationship between balloon diameter and dilatation pressure. Moreover, such balloons must be able to resist bursting at the relatively high pressures commonly employed during these procedures. Because commonly used lubricious catheter materials typically do not possess requisite elastomeric properties, the balloons are frequently prepared from a polymeric material that is different from, and is not readily bonded to, the material employed to fabricate the catheter. For, example, balloons are frequently formed from polyethylene terephthalate (PET), as well as nylon.

Catheters can include any number of internal lumens to provide functionalities to the distal end of the device. Typical lumens included within catheters include a guide wire lumen and an inflation lumen. Generally, the inflation lumen is configured to contain inflation medium and is in fluid communication with the balloons of the device.

According to the present invention, a catheter has been developed that can be used to treat any passage in the body in which it is desirable to control flow of biological fluids during the course of treatment. In preferred embodiments, the catheter can be used to provide one or more therapeutic agents to a treatment site that contains a valve, where it is desirable to maintain fluid flow through the treatment site in a physiologic direction during the course of treatment. More specifically, the catheter of the invention includes a valve to maintain bodily fluid flow in a single direction. The valve opens and closes with pressure and/or flow changes. The invention can be placed anywhere in the human (or animal) body where flow control is desired. As described herein, flow control at the treatment site can mean control both in direction of fluid flow and hemodynamics of that fluid flow. More specifically, the catheter provides the ability to maintain fluid flow in a physiologic direction (that is, block retrograde flow through the device). In addition, the catheter can preferably maintain proper hemodynamics at the treatment site by minimizing disruption of fluid flow patterns through the biological passage.

To facilitate the discussion of the invention, use of the invention to treat a heart valve will be addressed. Heart valves are selected because they provide the highest risk to the patient during treatment. Further, in terms of lowering the risk while providing a superior device, the advantages of this catheter can be clearly presented. However, it is understood that the device and methods disclosed are applicable to any valvular needs, for example, treatment of the esophagus or other biological passages of the body where controlled flow of biological fluids is desired during treatment. Additionally, the inventive device and methods are applicable to venous applications (such as, for example, failure of competence of venous valves).

A preferred use for this device is a method of treating a biological passage that contains a valve. It will be understood that the inventive device can be used at the location of the natural valve, or at a location adjacent to the natural valve to be treated. Moreover, the invention can be used to treat a native valve, or the invention can be used to treat an area surrounding and including a previously implanted prosthetic valve (for example, when therapeutic agent delivery is desirable after implantation of the prosthetic valve).

Figure 3:
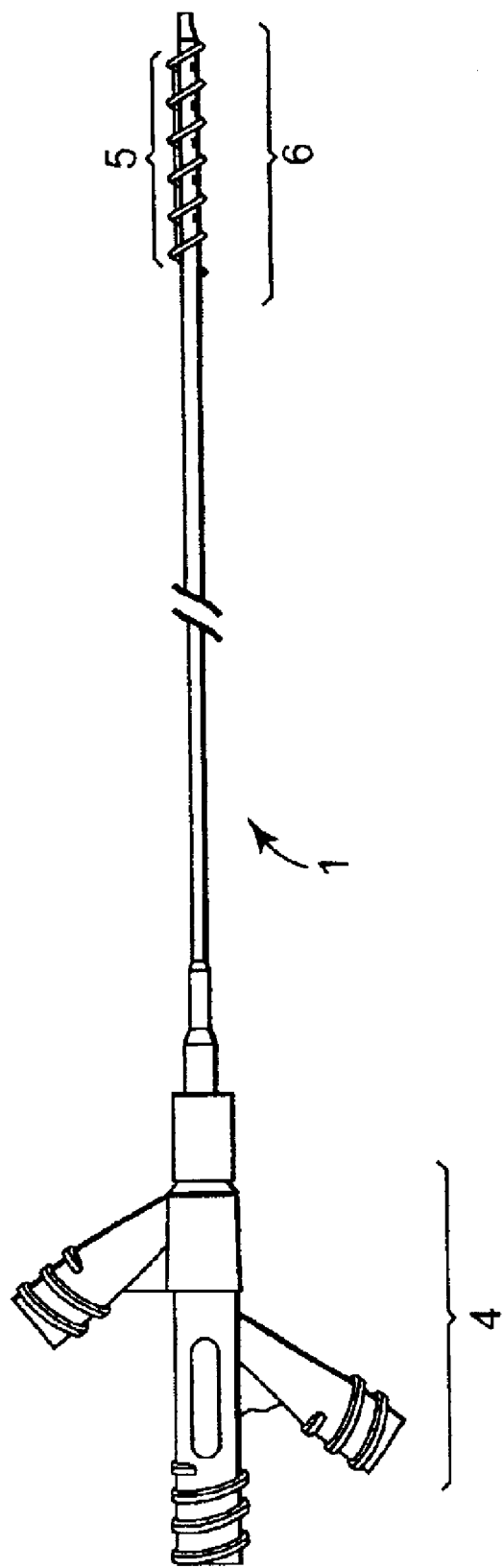
FIG. 3 is a perspective view of an embodiment of a catheter of the invention.
Figure 4:
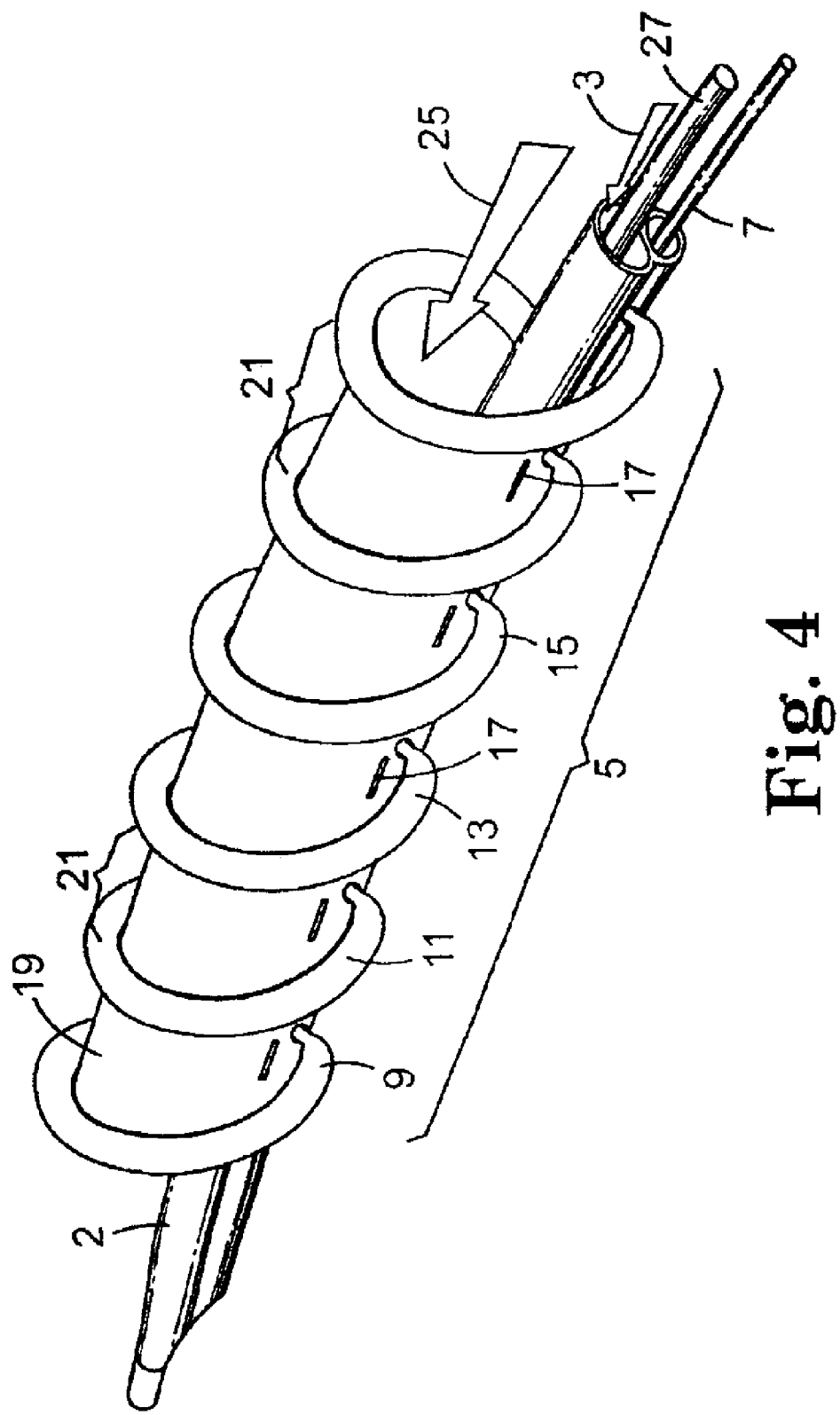
FIG. 4 is an exploded view in perspective of the distal portion of the embodiment shown in FIG. 3.

With reference to the accompanying FIGS., and initially to FIGS. 3 and 4, a catheter 1 in accordance with the invention is illustrated that includes a proximal end 4 and distal end 6. The catheter 1 is designed such that the distal end 6 is to be inserted into a patient to effect treatment at a treatment site. At the proximal end 4, controls are located to allow the interventionalist to control functionalities located at the distal end. The distal end 6 of the catheter includes an inflatable balloon assembly 5 for treatment of a valve (illustrated in an inflated state in FIGS. 3 and 4).

Referring to FIG. 3, the catheter 1 includes an inflatable balloon assembly 5 at the distal end 6. The balloon assembly 5 includes a single inflatable balloon member. In an uninflated state, the balloon assembly 5 does not significantly increase the overall diameter of the distal end 6 of the catheter 1. This allows the distal portion 6 of the catheter to be inserted into the patient and guided through the patient's vasculature to the desired treatment site. Once at the treatment site, the balloon assembly is inflated. When inflated, the balloon of the balloon assembly 5 impinges upon or engages the biological passage wall at the treatment site. The balloon assembly can include any number of individual balloons in a number of configurations, depending upon the particular treatment site. Some illustrative configurations of the balloon assembly will be described in more detail.

The inflatable balloon portions can be provided in a variety of configurations to engage the biological passage wall at the treatment site. For example, FIG. 4 illustrates one embodiment of the balloon assembly, wherein the balloon assembly 5 comprises a single piece of balloon tubing attached to the tubular member 2 to form toroidal or donut-shaped balloon portions 9, 11, 13, and 15. As shown in FIG. 4, the balloon tubing can be attached to the tubular member to form a helical configuration of the balloon portions 9, 11, 13, and 15.

Figure 5:
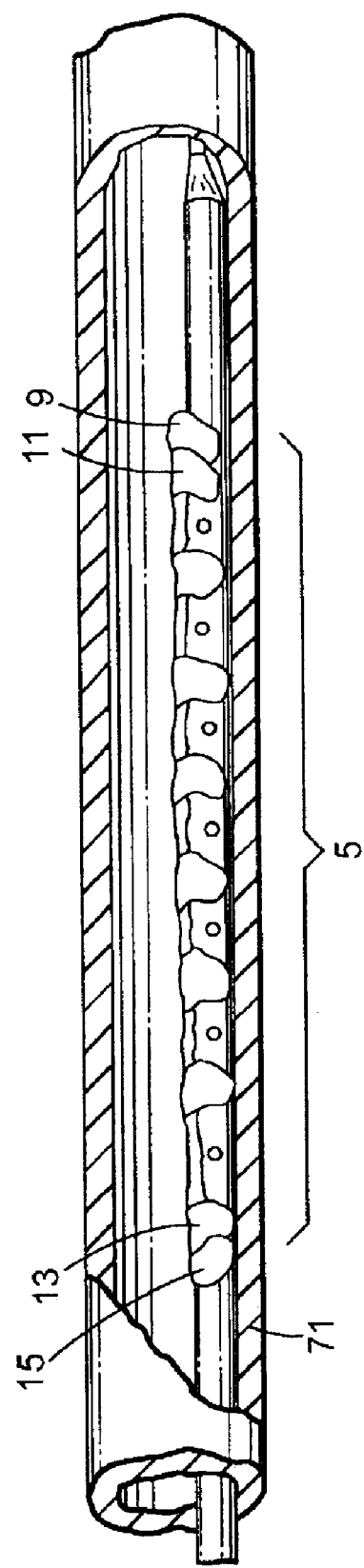
FIG. 5 is a side view of another embodiment of a catheter of the invention in a deflated state, shown within a biological passage.

Alternatively, the balloon portion(s) of the balloon assembly 5 can be provided in a non-helical configuration. FIG. 5 illustrates another embodiment of the balloon assembly, wherein the balloon assembly 5 comprises a single piece of balloon tubing attached to the tubular member 2 to form a series of toroidal shaped balloon portions 9, 11, 13, and 15. According to this embodiment, the most distal balloon portion 9 and the next most distal balloon portion 11 are positioned adjacent to each other, as are the most proximal balloon portion 15 and the next most proximal balloon portion 13. In this embodiment, pairing of the individual balloon portions at the proximal and distal ends of the balloon assembly advantageously provides two points of anchoring for each pair of balloon portions. As shown in FIG. 5, the balloon is in an uninflated state.

The inflatable balloon assembly is configured to impinge upon the walls of the treatment site to allow treatment of a valve while maintaining physiologic blood flow through the catheter. The number of individual balloon portions comprising the balloon assembly can thus be chosen to create a desired number of containment pockets described in more detail below. The individual balloon portions of the balloon assembly can be inflated from one or more points. Further, the spacing of the individual balloon portions can be modified as desired, to provide an effective amount of contact area with the biological passage wall for treatment. More balloon portions can be located between the previously described toroidal-shaped balloon portions 9, 11, 13 and 15, and the balloon assembly can be provided with a single proximal balloon portion and single distal balloon portion, as opposed to the dual anchoring assembly described previously. For all of these embodiments, the distance from the most proximal balloon portion to the most distal balloon portion of the balloon assembly can range from about 10 mm to about 30 mm apart, and the inside balloon portions can be disposed about 2 mm to about 3 mm apart.

In some embodiments, the balloon assembly can include multiple sections of inflatable balloon portions. For example, the mid-section of the balloon assembly can comprise balloon portions configured in a helical manner about the tubular member of the catheter, while the end sections of the balloon assembly can comprise plural distinct balloon portions configured in a non-helical manner about the tubular member. In this embodiment, the helical balloon portions can act to push the valve tissue evenly against the biological passage wall and allow proper function of the catheter valve.

In its inflated state, the balloon assembly defines a flow lumen 25 (also referred to herein as a perfusion lumen) that permits native biological fluid (such as blood) to continue to flow through the catheter 1 during treatment. As will be described in more detail below, the flow lumen 25 is defined by a sheath 19 that is attached to the balloon portions 9, 11, 13, and 15 of the balloon assembly. The individual balloon portions of the balloon assembly thus serve to expand the sheath 19 and create the flow lumen 25 of the catheter during use.

During use of the inventive device, the flow of blood through the sheath 19 can be cut off by one or more of the following: (1) a lesion in the biological passage can deform the sheath; (2) the device could be placed at a bend in a biological passage, causing the sheath to kink; or (3) the pressure of the fluid containing therapeutic agent could force the flow lumen of the catheter shut. The number of individual balloon portions comprising the balloon assembly, and the spacing between the individual balloon portions, can be important in maintaining the appropriate blood flow through the biological passage being treated. Therefore, the radial support for sheath 19 needed to maintain the blood flow lumen 25 through the center of the sheath 19 is provided by the inflatable balloon portions 9, 11, 13, and 15. The different configurations illustrated herein can be used to provide more or less radial support, as needed. Increasing the number of balloon portions in the balloon assembly can increase the ability of the balloon assembly to maintain the perfusion lumen 25 open.

The outside diameter of the inflatable balloon portions 9, 11, 13 and 15 in their inflated state is selected to create a suitably sized flow lumen 25 through the catheter, while also allowing a valve (described below) located within the flow lumen to control fluid flow through the catheter. In an exemplary embodiment, the balloon portions 9, 11, 13, and 15 are about 3 millimeters in outside diameter in their inflated form. The balloon portions, for example, can have an outside diameter ranging about 2 mm to about 22 mm in their uninflated state, depending upon the different biological passages of the human (or animal) body in which the inventive catheter will be used. The size of the balloon portions may also vary for different procedures and/or patients.

The balloon is preferably made of a polyolefin. One preferred polyolefin material is available from E.I DuPont de Nemours and Co. (Wilmington, Del.), under the trade name Surlyn® Ionomer.

An alternative embodiment of the balloon assembly is illustrated in FIGS. 9, 10, and 11, wherein the balloon assembly is formed by sealing an outer cylindrical sheath 51 and an inner cylindrical sheath 53 to each other at the ends of the sheaths. The cylindrical sheaths 51 and 53 are also intermittently sealed to one another at sections 55. An inflation region or pouch 57 is defined between the two sheaths 51 and 53. These seals 55 run along the circumference of the cylindrical sheaths 51 and 53, except that they are not complete in that spaces are left at certain points to allow the inflation medium to migrate from one pouch formed between the cylindrical sheaths 51 and 53 to another similar pouch.

As shown in FIGS. 9, 10 and 11, cutouts 59 can be provided in the proximal cone section 61 of the sheaths to allow blood to flow through the center of these sheaths 51, 53. At the proximal portion of the cone, the outer sheath 51 and the inner sheath 53 come to an outer balloon waist 61 and an inner balloon waist 63. The outer balloon waist 61 is bonded with an adhesive, such as Tracon®, to an outer shaft 65 and the inner balloon waist 63 is bonded with a similar adhesive to an inner shaft 67. The outer and inner shafts are made in a similar fashion to the embodiments described herein. The inner shaft 67 can define any number of lumens, for example a lumen for a guide wire 69, an inflation lumen, and the like.

According to this embodiment, the inflation medium and therapeutic agent medium are one and the same. When the balloon assembly is inflated, as shown in FIGS. 9, 10 and 11, the outer sheath 51 contacts the wall of the biological passage 71 at the areas designed by reference number 73. The contact area 73 is defined by the section of the outer sheath 51 that is not bonded to the inner sheath 53. The area 55 where the two sheaths 51, 53 are bonded, however, does not contact the wall of the biological passage 71. Therefore, a containment pocket or region 11 for the therapeutic agent is defined in the space between two adjacent contact areas 73. The outer sheath 51 can be provided with apertures or holes 75 in order to deliver the therapeutic agent to the wall of the biological passage 71 in the containment pocket 11. These apertures 75 allow for permeability of the inflation medium (which contains the therapeutic agent) out to the wall of the biological passage 71. Preferably, these apertures 75 are about 0.003 inches in diameter and spaced radially at 90° for each containment pocket 11. Here again other configurations can be suitable as well. For example, both the number and pattern of spacings of the apertures in each containment pocket 11 defined by adjacent inflation regions or pouches 57 can vary. The polymer used to make the outer sheath can either have the apertures 71 as discussed above or alternatively can be semi-permeable to the inflation/ therapeutic agent medium.

Similar to other embodiments described herein, the position and number of inflation pouches 57 can vary for different uses. To accomplish this, the seals between the two cylindrical sheaths 51, 53 can have different configurations depending upon what type of lifting and expansion force would be required by the desired application of the device.

The embodiment shown in FIGS. 9, 10 and 11 is preferably made by blowing two different sheaths, 51, 53, one slightly smaller than the other. The second smaller inner sheath 53 is inserted coaxially inside the outer sheath 51. These are then completely sealed distally, creating an occlusive seal 79 between the two sheaths 51, 53. These two sheaths 51, 53 can have intermittent seals through the body of the balloon assembly similar to what an inflatable air or water mattress would have; these seals are incomplete in places, allowing the inflation/therapeutic agent medium to flow throughout the device. In an exemplary embodiment, the seals are 2 to 3 mm apart with a 0.01 inch wide bond. On the proximal end in the cone area 61 of the sheaths 51, 53, there are sealed cutaway portions 59 for blood flow. This sealing is around the cutaway portions 59 and allows the blood to flow through cutaway portions 59 while still maintaining inflation space 79 in parts of the cone to the body of the cylindrical sheaths. The sealing can be accomplished in a number of different ways known in the art.

Other embodiments of the invention can employ seals in the balloon assembly that are intermittent forming welds that are similar to spot welds. In this embodiment, the therapeutic agent/inflation medium is one and the same, and the medium is delivered to into the balloon assembly and is delivered to the treatment site via apertures in the outer sheath. As with other embodiments described herein, the position and number of inflation pouches and/or seals can have multiple configurations depending upon the type of lifting and expansion force desired for a particular application.

Referring back to FIG. 4, the balloon assembly 5 further includes a cylindrical sheath 19 that connects the balloon portions 9, 11, 13, and 15. In use, when the balloon portions 9, 11, 13 and 15 are inflated, the balloon portions pull the sheath 19 into an expanded configuration, and the expanded sheath defines a flow lumen 25 that permits fluid flow through the device in a physiologic direction. Attached to the sheath and included within the flow lumen 25 is a valve 81 that permits physiologic flow of fluid (such as blood) through the device, while blocking retrograde flow.

The expanded diameter of the sheath 19 is less than the diameter of the balloon portions. Therefore, when the balloons are inflated, the sheath 19 is attached to the balloons at a point radially inward of the outer diameter of the balloons in order to create a containment pocket 21. Preferably, the sheath 19 is disposed through and connected to the interior portion of the toroidal-shaped balloon portions. In an exemplary embodiment, the sheath 19 is typically 25 mm from end to end longitudinally and is preferably about 0.001 inches thick.

In use, the sheath 19 is situated coaxially to a biological passage wall 71 (as shown in FIGS. 5–11) and is open at each end, thereby forming a passageway or flow lumen 25 for the blood to flow through when the balloon portions are inflated. Thus, the sheath 19 creates a barrier for separation of the fluid containing therapeutic agent and the blood. The sheath 19 is supported or held open by the toroidal-shaped balloon portions 9, 11, 13, and 15 and has the capability of having a relatively large expanded internal diameter. For example, the expanded internal diameter can be about 0.060 inches, providing a large volume of blood flow. This internal blood flow lumen 25 formed by the sheath 19 has the capability of being significantly larger than the tubular member 2.

In some embodiments, the geometry of the sheath 19 can be modified to provide flared or enlarged areas at the proximal end, distal end, or both the proximal and distal ends, of the sheath. This can optionally allow a tighter seal of the device around the treatment site (for example, the area surrounding the valve to be treated).

The sheath 19 can be prepared from a variety of polymeric materials that provide elastomeric properties. Preferably, the sheath 19 can be made of Surlyn® Ionomer. In an alternative preferred embodiment, the sheath 19 can be made of a polyester copolymer such as a random copolymer. The random copolymer used to make the sheath of the invention can be prepared according to standard procedures from ethylene glycol, and a mixture of dimethyl terephthalate and dimethyl isophthalate. As used in the random copolymer, the ratio of terephthalate to isophthalate in the random copolymer can be varied over the range of 99:1 to 80:20. Suitable copolymers are commercially available and are sold under the trade name Selar® PT, such as Selar® X257, available from E.I. Dupont de Nemours and Company (Wilmington, Del.). More preferably, the sheath is prepared from a material that does not inactivate the therapeutic agent being delivered, such as, for example, polypropylene, silicone, silicone-coated surfaces, PTFE, and the like.

The catheter of the invention allows biological fluid (such as blood) to flow through the device during treatment. This is accomplished by providing a flow lumen through the balloon assembly, so that when the balloon assembly is in its inflated state, the sheath 19 of the balloon assembly 5 defines a flow lumen 25 that permits blood flow therethrough. The flow lumen 25 further includes one or more valve(s) 81 that permit(s) blood flow in a physiologic direction while blocking retrograde flow (backflow) of the blood through the flow lumen 25.

In one embodiment, the flow lumen 25 is created by the inflation of the balloon portions 9, 11, 13, and 15 and can be subsequently collapsed upon deflation of the balloon portions 9, 11, 13, and 15 (FIG. 4). The dimensions of the deflated device will vary depending upon the specific use contemplated, but suitable sizes range 0.035 inches to 0.1 inches.

Thus, the blood flow lumen 25 is not an integral part of the shaft of the device of the invention. Rather, the flow lumen 25 is created by inflation of the balloon portions 9, 11, 13, and 15 of the device. Since the blood flow lumen 25 is not an integral part of the shaft, the ultimate diameter of the blood flow lumen 25 is not limited by the diameter of the tubular member 2. When the balloon portions 9, 11, 13, and 15 are deflated, the device is collapsed with essentially no blood flow lumen and is therefore small enough in diameter to be easily maneuvered through the patient's vascular system. Unlike prior art devices, when the balloon portions 9, 11, 13 and 15 are inflated, the cross-sectional area of the blood flow lumen 25 is a significant percentage of the cross-sectional area of the treatment site, such as a valvular area of the heart. It is believed that blood flow through the device is about 60% and can be as much as 80% of the blood flow through a healthy valvular area of the heart without the device in place.

With all of the embodiments described herein, because the flow lumen is created by the inflatable balloon assembly, blood flow is permitted through the flow lumen and the overall device can be kept to a minimal size. The flow lumen is formed upon inflation of the balloon assembly and the device is in effect collapsed in its uninflated form. This physical attribute allows the catheter to be of a small diameter when it is inserted into the patient's body and maneuvered to the desired position, yet provides a relatively large blood flow lumen when the balloon member is inflated. This inflatable flow lumen allows the size of the device to be minimized while the lumen for blood flow is maximized. Further, the containment pockets allow the therapeutic agent to be kept separate from physiologic blood flow, so that desired therapeutic agent can be administered at higher concentrations and locally at the selected treatment site.

The invention thus provides a catheter for treating a biological passage while maintaining blood flow through the device. In addition, the invention provides a device for delivering one or more therapeutic agents to the treatment site, while maintaining the therapeutic agent separate from blood flow through the device. This separation of the native biological fluid (blood) and therapeutic agent is accomplished by creation of one or more containment pockets using the balloon assembly of the device.

For purposes of the description herein, reference will be made to "therapeutic agent," but it is understood that the use of the singular term does not limit the application of therapeutics contemplated, and any number of therapeutic agents can be provided using the teaching herein. In one illustrative embodiment, the tubular member 2 of the catheter 1 includes a fluid delivery lumen 3 configured to contain therapeutic agent to be delivered to a treatment site. At its proximal end, the fluid delivery lumen 3 is coupled to a source of therapeutic agent (not shown). At its distal end, the fluid delivery lumen is in communication with containment pockets created by the device, as will now be described in more detail.

When inflated, the balloon portions 9, 11, 13 and 15 define a plurality of containment pockets 21 for containment of one or more therapeutic agents at the treatment site. As described herein, the containment pocket is a region in the biological passage that is isolated or separate from the fluid flowing through the flow lumen (for example, blood). Therefore, a fluid containing therapeutic agent can be contained in this containment pocket 21 in the desired concentrations for a predetermined period of time without entering the blood stream during that period of time. Any number of containment pockets can be provided by the device, as desired. The particular number of containment pockets 21 created by the catheter of the invention will depend upon the number of balloon portions contained within the balloon assembly.

As illustrated in FIG. 4, when the portions 9, 11, 13, and 15 are inflated, a containment pocket or region 21 is defined between (i) the sheath 19, (ii) the balloon portions 9, 11, 13, and 15 and, and (iii) a biological passage wall. When the balloon portions 9, 11, 13, and 15 are inflated, they in effect form a seal between the biological passage wall and the balloon portions 9, 11, 13, and 15. Thus the balloon portions define the outer boundary of the containment pocket 21. The sheath 19, which is attached to the balloon portions 9, 11, 13, and 15, defines the rest of the containment pocket 21. In some embodiments, when a single balloon is provided in a helical configuration about the tubular member 2, a continuous spiral containment pocket 21 will be formed by the device.

In use, therapeutic agent is carried from the fluid source (not shown), through fluid delivery lumen 3, and into containment pockets 21 through a plurality of apertures 17. The apertures 17 are placed longitudinally along the device between balloon portions 9, 11, 13, and 15. The apertures 17 are preferably placed on both sides of the tubular member 2 and preferably are positioned at an area that does not come in contact with the biological passage wall. Preferably, the apertures are configured to minimize damage to tissue at the treatment site. This can be accomplished by controlling one or more of such factors as the size, spacing, and location of the apertures so as to minimize the pressure of therapeutic agent as it leaves the apertures.

Preferably, the apertures 17 generally increase in diameter from proximal to distal end so that uniform flow out of each aperture 17 is achieved. The apertures are preferably sized such that the fluid containing therapeutic agent is not pressure injected out of the apertures 17, but rather the tissue at the treatment site is bathed with the fluid containing therapeutic agent. The size of the apertures will depend upon the pressure at which the fluid containing therapeutic agent is being provided at the proximal end by the therapeutic medium source (not shown). In an exemplary embodiment, the more proximal apertures 17 are about 0.003 inches in diameter and the more distal apertures are about 0.005 inches in diameter. These apertures 17 are placed about 2 to 3 mm apart from each other, as desired.

Preferably, the catheter minimizes tissue damage that can be caused by ejection of a high jet stream of a therapeutic agent from the catheter. Thus, the containment pocket 21 created between the sheath 19 and the biological passage wall 71 is preferably used to bathe the treatment site. In some embodiments, the containment pockets are filled with a porous material. In some embodiments, the use of a porous material in the containment pocket can provide enhanced delivery of the therapeutic agent to the treatment site. Examples of suitable porous material include porous polymers, polyethylene, polypropylene and the like.

Optionally, therapeutic agent can be delivered to the treatment site via protuberances that project from the catheter. Examples of suitable protuberances include needles, spikes, nozzles and microneedles. Protuberances can be provided by any component of the catheter that contacts the biological tissue of the treatment site when the balloon assembly is inflated, such as, for example, the sheath, one or more of the inflatable balloon portions, or the like.

Figure 6:
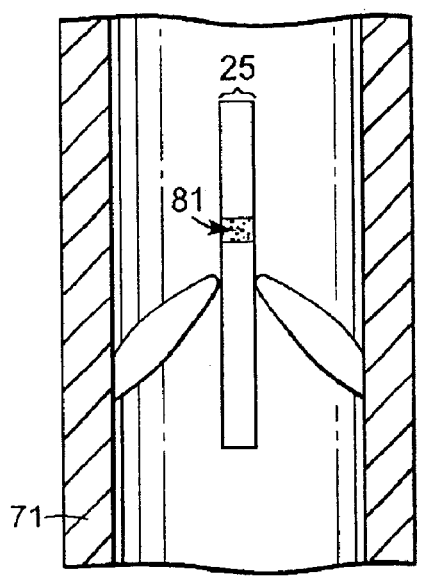
FIG. 6 is a cross-sectional view of a catheter of the invention, shown inserted in an uninflated state into a biological passage.
Figure 7:
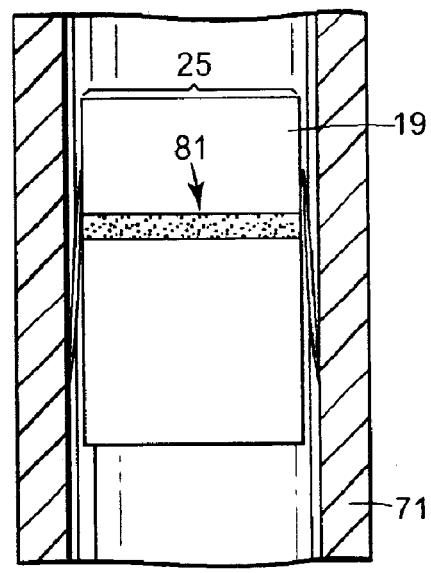
FIG. 7 is a cross-sectional view of the embodiment shown in FIG. 6, wherein the catheter is inserted into a biological passage and is in an inflated state.
Figure 8:
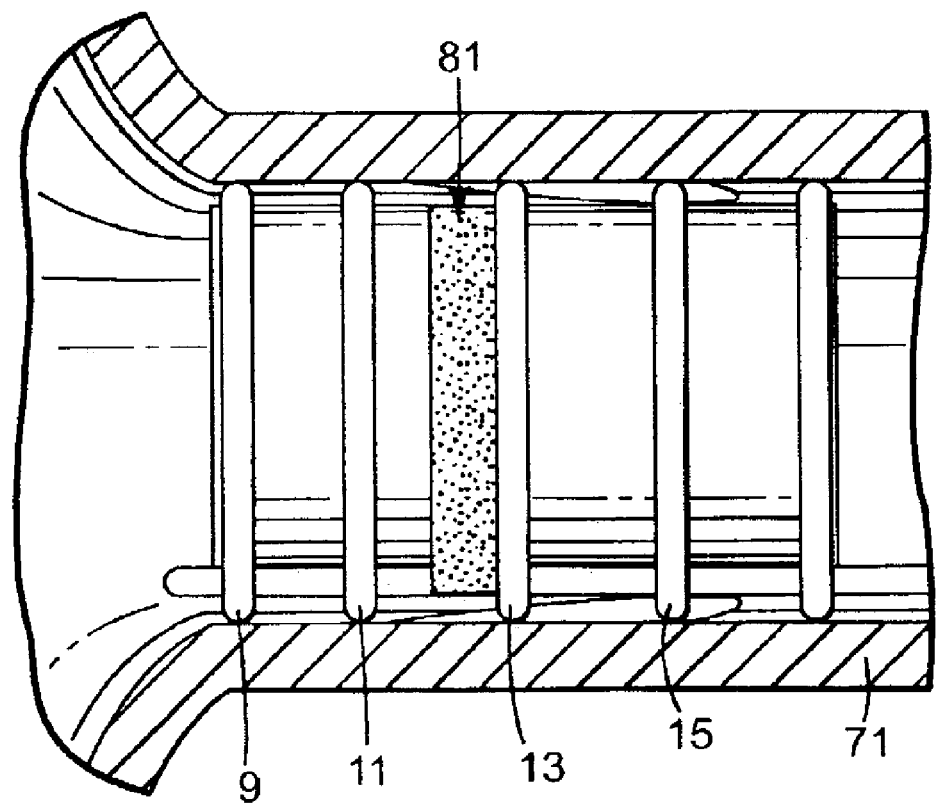
FIG. 8 is a cross-sectional view of the embodiment shown in FIG. 7.

The catheter of the invention advantageously provides at least one valve that provides the ability to control the direction of fluid flow through the device, as well as the hemodynamics of the fluid flow. More specifically, the valve allows blood flow at the treatment site in a physiologic direction, while effectively blocking retrograde flow (back flow). As illustrated in FIGS. 6–8, a preferred embodiment of the invention includes a valve 81 located within the inflatable balloon assembly 5. According to this embodiment, valve 81 is attached to the inner surface of sheath 19 and thus extends across the diameter of the flow lumen 25.

Prosthetic valves are well known, and it is understood that the valve of the inventive catheter can be provided in a number of embodiments. The valve is chosen to provide such physiologic characteristics as hemodynamic performance that approximates the natural state, and reduced risk of thrombogenicity. Preferably, the device complies with the natural motion of the tissue with which it is in contact, so that hemodynamics of the treatment site are maintained during a treatment period. The valve can be designed to allow blood flow in a physiologic direction (that is, forward flow of the blood through the biological passage), block back flow (also referred to as retrograde flow) of blood through the device, and collapse sufficiently to allow the catheter to be passed through the vasculature to the treatment site. Preferably, the components of the valve (for example, leaflets) are sufficiently flexible to open and close smoothly, with minimal pressure drop across the valve and without creating undue turbulence or hemolytically damaging the blood cells.

The valve is pre-sized to fit within the internal diameter of the sheath 19 and thus extend across the diameter of the flow lumen 25. The valve can thus be fabricated to any desired size, depending upon the particular application (for example, heart valve, or other biological passage in the body), and particular patient (for example, a young patient such as a young child, or an elderly patient).

Although FIGS. 6–8 illustrate valve 81 as being located along the length of the sheath 19, the valve 81 can be provided at any position within the sheath 19. For example, in some embodiments, positioning the valve in the proximal or distal end of the sheath can improve valve function and allow for a smaller collapsed profile. When the valve is located at a proximal or distal end of the sheath, the leaflets of the valve can extend beyond the sheath when the sheath is collapsed, thereby providing improved profile of the collapsed device. The position of the valve within the sheath can be such that it is positioned as closely as possible to the native valve's anatomical position, to provide improved valve function during treatment.

According to the invention, the valve is preferably configured to passively respond to differential pressures on either side of the valve. It is contemplated, however, that an active valve could be incorporated into the subject design that can further be controllable from the proximal catheter end. Generally, a valve according to the present invention comprises an occluder that is moved aside during forward flow of blood through the device, and blocks backflow through the lumen. The valve is preferably suitably durable to withstand pressures within the biological passage to be treated, but flexible enough to move within the device to allow blood flow through the flow lumen. Illustrative embodiments of the valve will now be described in more detail.

Figure 12:
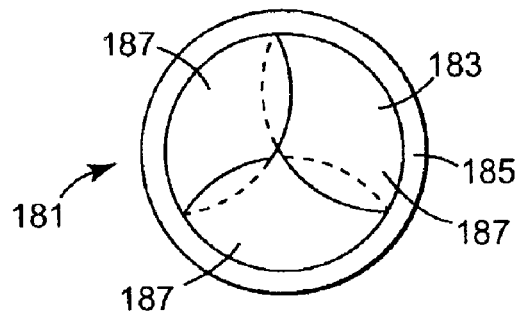
FIG. 12 is a top view of one embodiment of a valve of the invention.

As shown in FIG. 12, the valve can be provided in the form of a flexible leaflet valve 181. The valve shown in FIG. 12 is a tricuspid valve, and as such, it can be used to mimic the aortic valve. In this embodiment, the flexible leaflet valve 181 comprises a generally arcuate center portion 183 and, optionally a peripheral cuff portion 185. As illustrated, the center portion 183 of the valve 181 is generally arcuate in shape and comprises three leaflets 187 as shown, although it is understood that there could be any desired number of leaflets in the flexible valve, preferably, two to four leaflets. When the valve includes a peripheral cuff portion 185, this cuff portion can be used to attach the valve to the sheath, for example, by suturing, biocompatible adhesive, or other suitable attachment methods.

The flexible leaflet valve 181 is preferably disposed within the sheath 19 with the arcuate portion transverse of and at some acute angle relative to the plane of the walls of the sheath 19. The diameter of the arcuate portion can be substantially the same as the inside diameter of the lumen 25 when the balloon assembly is inflated. In this embodiment, the peripheral cuff portion 185 is disposed substantially parallel to the walls of the sheath 19. Thus, when the inflatable balloon assembly 5 is inflated, the valve 181 is expanded and spans the area of the flow lumen 25 of the device. Conversely, when the inflatable balloon assembly 5 is in a deflated state, the valve 181 preferably collapses within the balloon assembly so as to substantially conform to the outer dimensions of the collapsed balloon assembly. Thus, in a preferred embodiment, the peripheral cuff portion 185 is fabricated of a flexible material, to allow the cuff portion to collapse when the balloon assembly 5 is in an uninflated state. In this way, the valve does not significantly alter the overall diameter of the device. The peripheral cuff portion 185 can be fabricated of a suitable flexible material, and the material can be the same as, or different from, the material used to fabricate the leaflets of the valve.

In some embodiments of the invention, the leaflets of the valve can be attached to the sheath individually. In these embodiments, the peripheral cuff portion 185 is not included in the device. In these embodiments, the leaflets can be attached to the sheath using sutures, biocompatible adhesive, a combination of the two, or any other suitable attachment mechanism.

Alternatively, the valve can be fabricated to include standardized leaflet structures utilizing some of the methodologies described in U.S. Pat. No. 5,928,281 (the entire disclosure of which is incorporated herein by reference). According to this embodiment, a plurality of tissue leaflets are templated and attached together at their tips for a dimensionally stable and dimensionally consistent coapting leaflet subassembly. These valves are pre-aligned and stitched together to align the entire valve mating or seating surfaces at once. The desired number of tissue leaflets are obtained, and each leaflet is trimmed to the appropriate desired shape and size for the intended valve use using a template, defining a generally straight or linear coapting mating edge having opposing ends and a generally arcuate peripheral cusp extending therebetween. More particularly, each leaflet is placed on a cutting board and the selected template is then placed over the leaflet. Leaflet material extending beyond the boundaries of the template is then cut away using a cutting tool.

Once cut, the leaflets are pre-aligned along with the template. The leaflets are then attached or stitched together at one end. Although this reference further attaches this subassembly to a wireform and other structural components, for purposes of the present invention, the aligned leaflets can be used without additional structural material, and can be attached directly to the inner surface of the sheath 19, either using a peripheral cuff such as that shown in FIG. 12, or directly to the sheath 19 without additional structural components.

The material for the leaflets can be a synthetic resin foil in accordance with the state of the art, preferably a foil of flexible polyurethane. Other materials include silicones, Teflon™, and other polymers. The majority of the leaflet area consists of a thin membrane. In some embodiments, the area of the leaflets forming the commissural areas is more rigid, to provide added support for the valve leaflets. In some embodiments, mammalian tissue (such as porcine or bovine pericardium, or the like) can be used to form the leaflets.

Preferably, the material used to make the leaflets is matched so that all leaflets for fabricating a single valve, whether aortic, mitral, semilunar, or the like, are made of material having about the same resistance to stretching in the circumferential direction, that is, within about 10% of one another, or preferably within about 5% of one another.

Optionally, at least a portion of one or more of the leaflets can be inflatable. The leaflet or leaflets can be provided with an inflation lumen that is separate from, or the same as, the inflation lumen utilized for the inflatable balloon assembly. Such an inflatable leaflet or leaflets can be functionally connected with any inflation lumen by a flexible conduit or the like that also facilitates its movement away and back toward the collar. It will be appreciated that the provision of any number of catheter lumens can be constructed in accordance with well-known technique, and, as such, need not be discussed in more detail herein. In some embodiments, one or more of the leaflets are entirely inflated during application of the device. According to these embodiments, an inflated leaflet can create a better seal than leaflets that are not inflated. In some embodiments, only a portion of the leaflet is inflatable. According to these particular embodiments, partial inflation (for example, of the edge of the leaflet) can allow for control of mechanical properties of the leaflet and can lead to better function of the leaflet. Inflation of a portion or all of the leaflet or leaflets after placement of the catheter at a treatment site can allow the leaflet(s) to be compliant and smaller prior to placement of the device. When the leaflet(s) is in an uninflated state, therefore, the leaflet(s) would not significantly alter the overall dimensions of the inventive device. When the leaflet(s) is provided in an inflated state, during treatment of a biological passage, the leaflet(s) can be inflated to a desirable size to function as a replacement valve during the treatment period.

Optionally, the valve further comprises one or more cord-like structures to control or restrict leaflet motion. These cord-like structures can provide function similar to native chordae tendineae in the mitral and tricuspid valve assemblies. Preferably, these cord-like structures serve to attach the leaflets to the sheath 19 and prevent the leaflets from prolapsing during function of the valve. Suitable materials for fabricating these cord-like structures are durable to anchor the leaflets to the sheath, are sufficiently firm to provide support for the leaflets, and are sufficiently flexible to allow proper functioning of the valve according to the invention. The cord-like structures can be fabricated, for example, from such materials as Kevlar™, polyethylene, polyurethane, polypropylene, stainless steel, nitinol, and other like materials.

Figure 13:
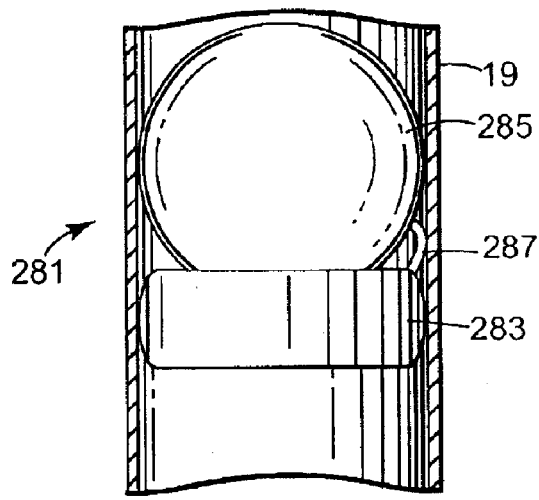
FIG. 13 is a side view of another embodiment of a valve of the invention.

As illustrated in FIG. 13, the valve can alternatively be provided in the form of a ball valve 281. According to this embodiment, the valve 281 comprises a collar 283 on the inner surface of the sheath 19 that slightly decreases the diameter of the flow lumen 25. At the distal side of the collar 283 is located a spherical occluder 285. The spherical occluder 285 is a blocking device, held in place by a tethering structure 287 that attaches the occluder 285 to the collar 283. One or more tethering structures can be provided to attach the spherical occluder to the collar. Examples of tethering structures include cords, wires, hinges, and other tethering mechanisms. Suitable materials for the tethering structure include Kevlar™, polyethylene, polyurethane, polypropylene, stainless steel, nitinol, and other like materials.

Alternatively, the spherical occluder 285 can be held in place using a mesh material (not shown). Preferably, the mesh material is fabricated from hemocompatible, non-thrombogenic material. In some embodiments, the mesh can be elastic to aid in the function of the valve. Suitable materials can be selected from those known in the art.

In use, the spherical occluder 285 is pushed aside by the forward flow of blood, but occludes the lumen of the collar 283 when blood flows backward. The function of the valve 281 thus mimics native valve function in that the valve 281 passively responds to pressure gradient changes on either side of the valve. The tethering structure 287 can be sufficiently elastic, for example, for maintaining the spherical occluder 285 in proximity to the collar 283 and for allowing the spherical occluder 285 to move away from the collar 283 when blood flows through the valve 281 a distance permitted by the length of the tethering structure 287. Otherwise, the tethering structure 287 can comprise non-extendible material for merely limiting movement away from the collar 283 as the spherical occluder 285 would move back and forth under influence of pressure changes. Any number of such tethering structures can be provided based upon desired opening and closing criterion and valve balance dynamics. Conversely, when the pressure gradient changes and the valve 281 closes in response to the pressure change, the spherical occluder 285 returns to the collar 283 and thereby occludes the lumen of the collar to prevent backflow of blood through the valve.

The spherical occluder 285 can be provided in the form of a ball, an ellipsoid, or any suitable shape that serves to occlude the collar 283 during use of the device.

In prior caged ball designs, there were several drawbacks associated with the primarily metal device. For example, one drawback seen with caged ball valves was that collisions with the occluder caused damage to blood cells in the valve area. Further, caged-ball valves were notorious for stimulating thrombosis, requiring patients to take lifelong prescriptions of anticoagulants. Further, the caged ball valve was constructed primarily of metal, and as such, provided a rigid valve structure that provided less than satisfactory hemodynamics at the treatment site.

In contrast, the ball valve 281 contemplated in one embodiment of the invention is contained within the sheath 19 of the catheter, and therefore the occluder 285 will not collide with walls of the biological passage being treated. Further, the ball valve 281 is used as a temporary functioning valve, during treatment of a biological passage only, and it is not meant to be permanently implanted within the patient. Therefore, risks associated with thrombosis are decreased compared with prior devices. Further, the ball valve 281 is fabricated primarily of polymeric materials (such as, for example, polyethylene, polyurethane, polystyrene, and the like) and therefore provides a more flexible valve structure that can more closely mimic native valve function.

The spherical occluder preferably comprises an inflatable device. The inflation lumen used to inflate the spherical occluder can be the same as, or different from, the inflation lumen used to inflate the balloon assembly 5. Such an inflatable occluder can be functionally connected with any inflation lumen by a flexible conduit or the like that also facilitates its movement away and back toward the collar. It will be appreciated that the provision of any number of catheter lumens can be constructed in accordance with well-known technique, and, as such, need not be discussed in more detail herein. When the spherical occluder is in an uninflated state, therefore, the occluder would not significantly alter the overall dimensions of the inventive device. When the spherical occluder is provided in an inflated state, during treatment of a biological passage, the spherical occluder can be inflated to a desirable size to function as a replacement valve during the treatment period.

Thus, in a preferred embodiment, the collar 283 is fabricated of a flexible material, to allow the collar to collapse when the balloon assembly 5 is in an uninflated state. In this way, the valve does not significantly alter the overall diameter of the device. The collar 283 can be fabricated of a suitable flexible material, and the material can be the same as, or different from, the material used to fabricate the spherical occluder of the valve.

Figure 14:
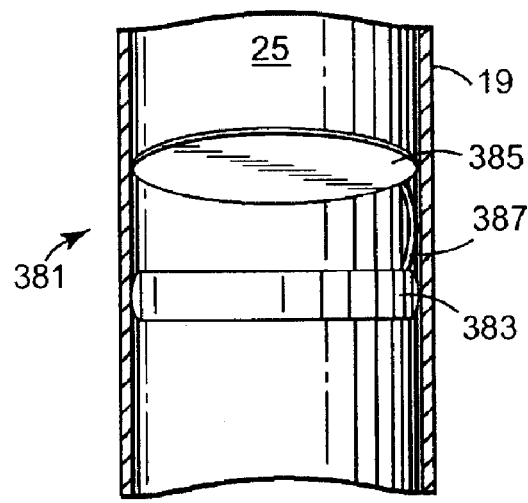
FIG. 14 is a side view of another embodiment of a valve of the invention.

In another embodiment, illustrated in FIG. 14, the valve can be provided in the form of a flap valve 381. According to this embodiment, the flap valve 381 comprises a collar 383 on the inner surface of the sheath 19. The collar 383 serves to decrease the diameter of the flow lumen 25. A flap 385 is attached to the distal side of the collar 383. The flap 385 is a blocking device, held in place by a tethering structure 387 that attaches the flap 385 to the distal side of collar 383. One or more tethering structures can be provided to attach the flap 385 to the collar in a similar sense as that described above for use with a spherical occluder 285.

In use, the flap 385 is pushed aside by the forward flow of blood, but occludes the lumen of the collar 383 when blood flows backward. Function of the flap 385 is similar to that described for the ball valve illustrated and described herein.

The flap 385 can be provided in the form of a disc, cone, or any suitable shape that serves to occlude the collar 383 during use of the device. Further, when the flap 385 is provided in the form of a disc, the disc can include one or more parts. As with all of the contemplated valve designs, it is preferable that the flap 385 also be expandable and collapsible with the sheath 19. In this regard, folding techniques, the use of elastic elements, and the like are contemplated.

When the catheter includes more than one flap 385, each disc can be separately attached to the collar 383. Optionally, one or more of the flaps can be inflatable. As described above for the leaflet valve, the flap(s) can be partially or totally inflatable. Reference is made to the prior discussion of leaflet valves for inflatable features. Optionally, the flap can be hinged at one point, to provide desired range of motion of the flap in use. Further, the flap can be designed from elastic materials, so that it occludes the lumen in its relaxed state (that is, when the flap occludes the lumen of the collar when blood flows backward).

In a preferred embodiment, the collar 383 is fabricated of a flexible material, to allow the collar to collapse when the balloon assembly 5 is in an uninflated state. In this way, the valve does not significantly alter the overall diameter of the device. The collar 383 can be fabricated of a suitable flexible material, and the material can be the same as, or different from, the material used to fabricate the flap(s) of the valve.

The invention provides a device and methods of providing therapeutic agent to a treatment site while maintaining proper flow of biological fluids through the treatment site, as well as isolating therapeutic agent from the flow of native biological fluids through the device. The therapeutic agent is provided to the treatment site in a therapeutically effective amount and concentration for the desired treatment. For example, 100 mcg/ml of heparin can be used as disclosed in "Effect of Controlled Adventitial Delivery on Smooth Muscle Cell Proliferation: by Edelman et al., Proc. Natl. acad. Sic. (USA) 1990; 87:3773–3778, which is incorporated herein by reference. Another exemplary therapeutic agent is one or more decalcifying agents, for example, sodium-EDTA (sodium-ethylenediaminetetraacetic acid).

The therapeutic agent is provided at a pressure ranging from a minimal value over local blood pressure to 50 pound per square inch (psi), depending upon the volume and concentration of therapeutic agent desired. Other pressures are contemplated for other uses as per the flexible nature of this device.

The blood in the biological passage continues to flow through the flow lumen created through the center of the sheath. Since the flow lumen created through the sheath is relatively large (compared to the size of the biological passage), the interruption of blood flow through the biological passage is minimized. Further, since the blood flow is isolated from the containment pocket, the therapeutic agent is only administered locally and does not enter the blood stream until the balloons are deflated (if at all). This allows for the therapeutic agent to be provided to the biological passage wall in high concentrations without providing a high concentration of the therapeutic agent in the bloodstream. After the therapeutic agent has been administered to the biological passage wall for the desired time, the device is removed. Because of the large volume of blood flow accommodated by this invention, numerous applications of the therapeutic agent can be effected without removing the therapeutic agent delivery device for a relatively long period of time, for example, for 15 minutes.

The invention thus provides a catheter that provides an interventionalist with flexibility as to the duration of treatment of a valvular site, the amount and type of therapeutic agent administered directly to the site (without concerns associated with systemic delivery), and the number of administrations of therapeutic agents (either simultaneously (as in the case of a single medium carrying more than one therapeutic agents) or sequentially (as in the case of multiple administrations of single therapeutic agents).

As used herein, "therapeutic agent" refers to an agent that affects physiology of biological tissue. In a broad sense, therapeutic agents can be non-genetic agents, genetic agents, or cellular material.

Examples of non-genetic therapeutic agents include, but are not limited to, anti-thrombogenic agents, anti-proliferative agents, anti-inflammatory agents, antineoplastic agents, anesthetic agents, anti-coagulants, vascular cell growth promoters, vascular cell growth inhibitors, decalcifying agents, and cholesterol-lowering agents.

Examples of anti-thrombogenic agents include heparin, heparin derivatives, urokinase, and PPack (dextrophenylalanine proline arginine chloromethylketone).

Examples of anti-proliferative agents include enoxaprin, angiopeptin, monoclonal antibodies capable of blocking smooth muscle cell proliferation, hirudin, and acetylsalicylic acid.

Examples of anti-inflammatory agents include dexamethasone, prednisolone, corticosterone, budesonide, estrogen, sulfasalazine, and mesalamine.

Examples of antineoplastic agents include paclitaxel, 5-fluorouracil, ciplatin, vinblatine, vincristine, epothilones, endostatin, angiostatin, and thymidine kinase inhibitors.

Examples of anesthetic agents include lidocaine, bupivacaine, and ropivacaine.

Examples of anti-coagulants include D-Phe-Pro-Arg chloromethylketone, an RGD peptide-containing compound, heparin, antithrombin compounds, platelet receptor antagonists, anti-thrombin antibodies, anti-platelet receptor antibodies, acetylsalicylic acid, prostaglandin inhibitors, platelet inhibitors and tick antiplatelet peptides.

Examples of vascular cell growth promoters include growth factor inhibitors, growth factor receptor antagonists, transcriptional activators, and translational promoters.

Examples of vascular cell growth inhibitors include growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin.

Examples of decalcifying agents include ethylenediaminetetraacetic acid (EDTA) and the like.

Examples of cholesterol-lowering agents include vasodilating agents and agents that interfere with endogenous vasoactive mechanisms.

In some embodiments, the therapeutic agent can comprise genetic material. For purposes of the present invention, genetic material includes nucleic acid, such as DNA or RNA, that encodes an agent or molecule of interest. For example, the genetic material can include anti-sense DNA or RNA. Alternatively, the genetic material can include DNA coding for any of the following: anti-sense RNA, tRNA or rRNA to replace defective or deficient endogenous molecules, angiogenic factors, cell cycle inhibitors (including cell differentiation inhibitors and the like), agents that interfere with cell proliferation (including thymidine kinase and the like), and bone morphogenic proteins. Examples of angiogenic factors include, but are not limited to, growth factors such as acidic and basic fibroblast growth factors, vascular endothelial growth factor, epidermal growth factor, transforming growth factor α and β, platelet-derived endothelial growth factor, platelet-derived growth factor, tumor necrosis factor α, hepatocyte growth factor, and insulin like growth factor.

Examples of bone morphogenic proteins (BMP) include, but are not limited to BMP-2, BMP-3, BMP-4, BMP-5, BMP-6 (Vgr-1), BMP-7 (OP-1) BMP-8, BMP-9, BMP-10, BMP-11, BMP-12, BMP-13, BMP-14, BMP-15, AND BMP-16. Preferred bone morphogenic proteins include BMP-2, BMP-3, BMP-4, BMP-5, BMP-6, and BMP-7. These dimeric proteins can be provided as homodimers, heterodimers, or combinations thereof, alone or together with other molecules. Alternatively, or in addition, molecules capable of inducing an upstream or downstream effect of a bone morphogenic protein can be provided. Such molecules include any of the "hedgehog" proteins, or the nucleic acid encoding them.

In some embodiments, the therapeutic agent can comprise cellular material. Such cellular material can be of human origin (autologous or allogeneic) or from an animal source (xenogeneic). The cellular material can comprise genetically engineered material designed to deliver proteins of interest at the treatment site.

Exemplary cellular material includes stem and progenitor cells, including side population cells, lineage negative cells (lin−), bone marrow derived stem cells such as CD34+ and CD34− cells, cKit+ cells, mesenchymal stem cells, embryonic stem cells, fetal or neonatal cells, cord blood cells, cardiac-derived stem cells, fat-derived stem cells, and endothelial progenitor cells. Other exemplary cells include cells from whole blood marrow; bone marrow mononuclear cells; muscle-derived cells such as skeletal myoblasts (satellite cells), adult cardiomyocytes, "go cells", and other muscle-derived cells (MDCs); endothelial cells; fibroblasts (for example, myoD scar fibroblasts); smooth muscle cells; genetically modified cells such as pacing cells; cloned cells such as embryonic stem cell clones; immunologically masked cells; teratoma-derived cells, and cell populations that have been treated with differentiation or growth factors, such as mesenchymal cells or fibroblasts that have been treated with 5-aza. Also included are tissue engineered grafts, for example isolated cells that have been grafted onto resorbable scaffolds such as collagen or PLGA.

The delivery medium used to deliver the therapeutic agent to the treatment site can be suitably formulated to maintain or enhance the activity of the therapeutic agent. For example, when the therapeutic agent comprises cellular material, the delivery medium can be formulated to maintain cell function and viability.

Alternatively, the therapeutic agent can be contained within a medium that is coated on at least a portion of the surface of the device that will contact the tissue at the treatment site. For example, the therapeutic agent can be contained within a suitable polymer coating that provides release of the therapeutic agent during treatment. In one embodiment, at least a portion of the surface of the catheter that will contact tissue is coated with a swellable hydrogel polymer coating as described in U.S. Pat. No. 6,409,716 ("Drug Delivery," Sahatjian et al., co owned by the assignee of the present application, and incorporated herein by reference in its entirety). As described therein, the hydrogel is a cross-linked polymer material formed from the combination of a colloid and water. Cross-linking reduces solubility and produces a jelly-like polymer that is characterized by the ability to swell and absorb a substantial amount of the therapeutic agent of interest, typically in aqueous solution form. The hydrogel coating is also particularly hydrophilic, water swellable, and lubricious. The aqueous therapeutic agent solution can be effectively squeezed out of the coating when pressure is applied by inflation of the balloon portions of the inventive catheter.

The present invention is not limited to the above-described preferred methods, devices, systems and apparatuses. Furthermore, it should be understood that, while particular embodiments of the invention have been discussed, this invention is not limited thereto, as modifications can be made by those skilled in the art, particularly in light of the foregoing teachings. Accordingly, the appended claims contemplate coverage of any such modifications that incorporate the essential features of these improvements within the true spirit and scope of the invention.

What is claimed is:

1. A catheter for insertion into a biological passage which contains a first flowing fluid already in the biological passage, the catheter comprising:
   a. a tubular member having a proximal end and a distal end;
   b. a fluid delivery lumen contained within the tubular member;
   c. an inflatable balloon assembly disposed at the distal end of the tubular member, the balloon assembly including an inflatable balloon member having an uninflated state and an inflated state, the balloon assembly including apertures in communication with the fluid delivery lumen;
   d. an inflation lumen in communication with the balloon member; and
   e. a valve contained within the inflatable balloon assembly, the inflatable balloon assembly configured such that when the balloon member is in the inflated state: (i) sections of the balloon member contact the biological passage defining at least one containment pocket; (ii) the apertures are disposed in the containment pocket, (iii) a flow lumen is defined through the balloon member to allow the first fluid already in the biological passage to flow through the balloon member; and (iv) the valve functions to allow the first flowing fluid already in the biological passage to flow through the flow lumen in a physiologic direction, while blocking backflow of the first fluid through the flow lumen.

2. The catheter according to claim 1 further comprising a guide wire lumen contained within the tubular member.

3. The catheter according to claim 1 wherein the valve is a leaflet valve.

4. The catheter according to claim 3 wherein the leaflet valve is inflatable.

5. The catheter according to claim 3 wherein the leaflet valve comprises three leaflets.

6. The catheter according to claim 3 wherein the leaflet valve comprises two leaflets.

7. The catheter according to claim 1 where the valve is a ball valve.

8. The catheter according to claim 7 wherein the ball valve is inflatable.

9. The catheter according to claim 1 wherein the valve is a flap valve.

10. The catheter according to claim 9 wherein the flap valve is inflatable.

11. The catheter according to claim 1 further comprising a therapeutic agent containing medium provided to one or more of the containment pockets.

12. The catheter according to claim 11 wherein the medium comprises a hydrogel.

13. The catheter according to claim 11 wherein the medium comprises a polyacrylic acid.

14. The catheter according to claim 11 wherein the medium comprises a copolymer of polylactic acid and polycaprolactone.

15. The catheter according to claim 1 wherein the balloon assembly comprises a single balloon attached to the tubular member to form a helical configuration about the tubular member.

16. A catheter for insertion into a biological passage which contains a first flowing fluid, already in the biological passage, the catheter comprising:
   a. a tubular member having a proximal end and a distal end;
   b. an inflatable balloon assembly disposed at the distal end of the tubular member, the balloon assembly including an inflatable balloon member having an uninflated state and an inflated state,
   c. an inflation lumen in communication with the balloon member;
   d. a valve contained within the inflatable balloon assembly,
   the inflatable balloon assembly configured such that when the balloon member is in the inflated state: (i) sections of the balloon member contact the biological passage defining at least one containment pocket; (ii) a flow lumen is defined through the balloon member to allow the first fluid already in the biological passage to flow through the balloon member; and (iii) the valve functions to allow the first flowing fluid already in the biological passage to flow through the flow lumen in a physiologic direction, while blocking backflow of the first fluid through the flow lumen.

17. The catheter according to claim 16 wherein the inflation lumen is configured to contain a medium comprising one or more therapeutic agents.

18. The catheter according to claim 16 wherein the valve is a leaflet valve.

19. The catheter according to claim 18 wherein the leaflet valve is inflatable.

20. The catheter according to claim 18 wherein the leaflet valve comprises three leaflets.

21. The catheter according to claim 18 wherein the leaflet valve comprises two leaflets.

22. The catheter according to claim 16 where the valve is a ball valve.

23. The catheter according to claim 22 wherein the ball valve is inflatable.

24. The catheter according to claim 16 wherein the valve is a flap valve.

25. The catheter according to claim 24 wherein the flap valve is inflatable.

26. A catheter for insertion into a biological passage which contains a first flowing fluid already in the biological passage, the catheter comprising:
   a. a tubular member having a proximal end and a distal end;
   b. a fluid delivery lumen contained within the tubular member;
   c. an inflatable balloon assembly comprising a first toroidal-shaped balloon disposed at the distal end of the tubular shaft, a second toroidal-shaped balloon spaced proximally from the first toroidal-shaped balloon, and a cylindrical sheath attached to the first and second toroidal-shaped balloons, wherein the first and second toroidal shaped balloons have an outer diameter, and wherein the sheath is attached to the toroidal-shaped balloons at a position radially inward of the outer diameter of the toroidal-shaped balloons;
   d. an inflation lumen in communication with the toroidal-shaped balloons;

e. a valve contained within the sheath, wherein the inflatable balloon assembly is configured such that when the toroidal-shaped balloons are inflated: (i) the toroidal-shaped balloons expand the sheath, (ii) sections of the toroidal-shaped balloons contact the biological passage wall defining at least one containment pocket between the biological passage, the tubular shaft, the toroidal-shaped balloons, and the sheath; (iii) the apertures are disposed in the containment pocket, (iv) the sheath forms a flow lumen to allow the first fluid already in the biological passage to flow through the balloon member; and (v) the valve functions to allow the first flowing fluid already in the biological passage to flow through the flow lumen in a physiologic direction, while blocking backflow of the first fluid through the flow lumen.

27. A method of delivering a therapeutic fluid to a treatment site in a biological passage, the treatment site including a valve, the biological passage containing a first fluid, the method comprising steps of:

a. providing an inflatable balloon assembly on the distal end of a catheter, the size of the balloon assembly when deflated adapted to fit within the biological passage;

b. positioning the balloon assembly at the treatment site;

c. inflating the balloon assembly at the treatment site;

d. engaging a section of the biological passage with a section of the balloon assembly while maintaining a section of the balloon assembly away from the biological passage thereby defining a plurality of containment pockets within the engaging section;

e. delivering a therapeutic fluid to the containment pockets, wherein when the balloon assembly is inflated, the balloon assembly defines a flow lumen through which the first fluid already in the biological passage can flow, while maintaining the therapeutic fluid within the containment pockets, and a valve contained within the balloon assembly functions to allow the first flowing fluid already in the biological passage to flow through the balloon member in a physiologic direction, while blocking backflow of the first fluid through the balloon member.

28. The method according to claim 27 further comprising the step of inflating the valve after positioning the balloon assembly at the treatment site.

\* \* \* \* \*